United States Patent
Xu et al.

(10) Patent No.: US 9,370,160 B2
(45) Date of Patent: *Jun. 21, 2016

(54) TOBACCO INBRED PLANTS ALBEX1F AND ALBEX1MS

(75) Inventors: Dongmei Xu, Glen Allen, VA (US); Mark T. Nielsen, Nicholasville, KY (US); Yanxin Shen, Glen Allen, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/406,169

(22) Filed: Feb. 27, 2012

(65) Prior Publication Data

US 2012/0222689 A1 Sep. 6, 2012

Related U.S. Application Data

(63) Continuation-in-part of application No. 11/611,782, filed on Dec. 15, 2006.

(60) Provisional application No. 61/507,732, filed on Jul. 14, 2011, provisional application No. 61/447,487, filed on Feb. 28, 2011.

(51) Int. Cl.
*A01H 5/12* (2006.01)
*A24B 15/10* (2006.01)
*C12N 9/02* (2006.01)
*C12N 15/82* (2006.01)

(52) U.S. Cl.
CPC ............ *A01H 5/12* (2013.01); *A24B 15/10* (2013.01); *C12N 9/0073* (2013.01); *C12N 15/8243* (2013.01)

(58) Field of Classification Search
None
See application file for complete search history.

(56) References Cited

U.S. PATENT DOCUMENTS

| | | |
|---|---|---|
| 4,693,976 A | 9/1987 | Schilperoort et al. |
| 4,732,856 A | 3/1988 | Federoff |
| 4,762,785 A | 8/1988 | Comai |
| 4,801,540 A | 1/1989 | Hiatt et al. |
| 4,940,838 A | 7/1990 | Schilperoort et al. |
| 4,945,050 A | 7/1990 | Sanford et al. |
| 5,004,863 A | 4/1991 | Umbeck |
| 5,013,658 A | 5/1991 | Dooner et al. |
| 5,034,323 A | 7/1991 | Jorgensen et al. |
| 5,104,310 A | 4/1992 | Saltin |
| 5,107,065 A | 4/1992 | Shewmaker et al. |
| 5,141,131 A | 8/1992 | Miller et al. |
| 5,149,645 A | 9/1992 | Hoekema et al. |
| 5,159,135 A | 10/1992 | Umbeck |
| 5,177,010 A | 1/1993 | Goldman et al. |
| 5,231,019 A | 7/1993 | Paszkowski et al. |
| 5,302,523 A | 4/1994 | Coffee et al. |
| 5,352,605 A | 10/1994 | Fraley et al. |
| 5,378,619 A | 1/1995 | Rogers |
| 5,384,253 A | 1/1995 | Krzyzek et al. |
| 5,463,174 A | 10/1995 | Moloney et al. |
| 5,464,763 A | 11/1995 | Schilperoort et al. |
| 5,464,765 A | 11/1995 | Coffee et al. |
| 5,469,976 A | 11/1995 | Burchell |
| 5,472,869 A | 12/1995 | Krzyzek et al. |
| 5,583,021 A | 12/1996 | Dougherty et al. |
| 5,595,733 A | 1/1997 | Carswell et al. |
| 5,614,399 A | 3/1997 | Quail et al. |
| 5,641,664 A | 6/1997 | D'Halluin et al. |
| 5,668,295 A | 9/1997 | Wahab et al. |
| 5,679,558 A | 10/1997 | Göbel et al. |
| 5,684,241 A | 11/1997 | Nakatani et al. |
| 5,712,135 A | 1/1998 | D'Halluin et al. |
| 5,713,376 A | 2/1998 | Berger |
| 5,766,900 A | 6/1998 | Shillito et al. |
| 5,929,304 A | 7/1999 | Radin et al. |
| 6,002,070 A | 12/1999 | D'Halluin et al. |
| 6,074,877 A | 6/2000 | D'Halluin et al. |
| 6,907,887 B2 | 6/2005 | Conkling |
| 6,953,040 B2 | 10/2005 | Atchley et al. |
| 6,965,062 B2 * | 11/2005 | Rufty .................. 800/317.3 |
| 7,032,601 B2 | 4/2006 | Atchley et al. |
| 7,700,834 B2 | 4/2010 | Xu et al. |
| 7,700,851 B2 | 4/2010 | Xu |
| 7,812,227 B2 | 10/2010 | Xu |
| 7,855,318 B2 | 12/2010 | Xu |
| 7,884,263 B2 * | 2/2011 | Dewey et al. .................. 800/285 |
| 8,058,504 B2 | 11/2011 | Xu |
| 8,124,851 B2 * | 2/2012 | Dewey et al. .............. 800/317.3 |
| 8,319,011 B2 * | 11/2012 | Xu ............................. A01H 5/12 131/271 |
| 2002/0042934 A1 | 4/2002 | Staub et al. |

(Continued)

FOREIGN PATENT DOCUMENTS

EP 0 120 516 A3 10/1984
EP 0 267 159 A3 5/1988

(Continued)

OTHER PUBLICATIONS

Julio, E. et al. Molecular Breeding (2008), vol. 21, pp. 369-381.*
Nikova, V. et al. Euphytica (1997), vol. 94, pp. 375-378.*
Siminszky, B. et al. PNAS (Oct. 11, 2005), vol. 102, No. 41 pp. 14919-14924.*
McCallum, C. et al. (Apr. 2000) Nature, vol. 18; pp. 455-457.*
Wernsman, E. et al. Tobacco Science (1970); vol. 14, pp. 34-36.*
U.S. Appl. No. 60/337,684, Xu, filed Nov. 13, 2001.
U.S. Appl. No. 60/347,444, Xu, filed Jan. 11, 2002.
U.S. Appl. No. 60/363,684, Xu, filed Mar. 12, 2002.
U.S. Appl. No. 60/418,933, Xu, filed Oct. 16, 2002.
U.S. Appl. No. 60/485,368, Xu, filed Jul. 8, 2003.
U.S. Appl. No. 60/503,989, Xu, filed Sep. 18, 2003.
U.S. Appl. No. 60/566,235, Xu, filed Apr. 29, 2004.

(Continued)

Primary Examiner — Russell Kallis
(74) Attorney, Agent, or Firm — Arnold & Porter LLP

(57) ABSTRACT

The present invention provides tobacco inbred plants ALBEX1F and ALBEX1MS. The present invention also provides parts of such plants and products made from those parts. The present invention also includes progeny of the provided plants including hybrids.

21 Claims, No Drawings

(56) References Cited

U.S. PATENT DOCUMENTS

| | | | |
|---|---|---|---|
| 2004/0103449 A1 | 5/2004 | Xu | |
| 2004/0111759 A1 | 6/2004 | Xu | |
| 2004/0117869 A1 | 6/2004 | Xu | |
| 2004/0162420 A1 | 8/2004 | Xu | |
| 2005/0132444 A1 | 6/2005 | Xu | |
| 2005/0160493 A9 | 7/2005 | Ratcliffe et al. | |
| 2005/0178398 A1 | 8/2005 | Breslin et al. | |
| 2005/0223442 A1 | 10/2005 | Xu | |
| 2005/0244521 A1 | 11/2005 | Strickland et al. | |
| 2006/0037096 A1 | 2/2006 | Xu | |
| 2006/0037623 A1 | 2/2006 | Lawrence | |
| 2006/0041949 A1 | 2/2006 | Xu | |
| 2006/0157072 A1 | 7/2006 | Albino et al. | |
| 2006/0185686 A1 | 8/2006 | Lawrence | |
| 2006/0191548 A1 | 8/2006 | Strickland et al. | |
| 2007/0149408 A1 | 6/2007 | Thomas et al. | |
| 2007/0199097 A1* | 8/2007 | Xu et al. | 800/278 |
| 2007/0292871 A1 | 12/2007 | Xu | |
| 2008/0076126 A1 | 3/2008 | Xu | |
| 2008/0202541 A1 | 8/2008 | Dewey et al. | |
| 2008/0245377 A1 | 10/2008 | Marshall et al. | |
| 2009/0119788 A1 | 5/2009 | Mallmann et al. | |
| 2009/0205072 A1 | 8/2009 | Dewey et al. | |
| 2010/0218270 A1 | 8/2010 | Xu et al. | |
| 2010/0235938 A1 | 9/2010 | Xu et al. | |
| 2010/0235945 A1 | 9/2010 | Xu et al. | |
| 2010/0235952 A1 | 9/2010 | Xu et al. | |
| 2011/0048437 A1 | 3/2011 | Xu | |
| 2011/0078817 A1 | 3/2011 | Xu | |
| 2011/0174322 A1 | 7/2011 | Dewey et al. | |
| 2011/0263328 A1 | 10/2011 | Yamashita et al. | |
| 2012/0117933 A1 | 5/2012 | Dewey et al. | |
| 2012/0118308 A1 | 5/2012 | Dewey et al. | |

FOREIGN PATENT DOCUMENTS

| | | |
|---|---|---|
| EP | 0 292 435 B1 | 11/1988 |
| EP | 0 320 500 B1 | 6/1989 |
| EP | 0 116 718 B1 | 5/1990 |
| EP | 0 159 418 B1 | 5/1990 |
| EP | 0 176 112 B1 | 5/1990 |
| EP | 0 131 624 B1 | 9/1992 |
| EP | 0 627 752 B1 | 7/1997 |
| EP | 1 033 405 A3 | 9/2000 |
| EP | 0 290 799 B9 | 11/2003 |
| WO | WO 87/06614 A1 | 11/1987 |
| WO | WO 92/09696 A1 | 6/1992 |
| WO | WO 93/21335 A2 | 10/1993 |
| WO | WO 94/01930 A1 | 1/1994 |
| WO | WO 00/67558 A1 | 11/2000 |
| WO | WO 02/072758 A2 | 9/2002 |
| WO | WO 02/100199 A2 | 12/2002 |
| WO | WO 03/078577 A2 | 9/2003 |
| WO | WO 2004/035745 A2 | 4/2004 |
| WO | WO 2005/038018 A2 | 4/2005 |
| WO | WO 2005/038033 A2 | 4/2005 |
| WO | WO 2005/046363 A2 | 5/2005 |
| WO | WO 2005/111217 A2 | 11/2005 |
| WO | WO 2005/116199 A2 | 12/2005 |
| WO | WO 2006/022784 A1 | 3/2006 |
| WO | WO 2006/091194 A1 | 8/2006 |
| WO | WO 2006/120570 A2 | 11/2006 |
| WO | WO 2008/070274 A2 | 6/2008 |
| WO | WO 2008/076802 A2 | 6/2008 |
| WO | WO 2009/064771 A2 | 5/2009 |
| WO | WO 2011/088180 A1 | 7/2011 |
| WO | WO 2012/118779 A1 | 9/2012 |
| WO | WO 2014/110363 A1 | 7/2014 |

OTHER PUBLICATIONS

U.S. Appl. No. 60/607,357, Xu, filed Sep. 3, 2004.
U.S. Appl. No. 60/646,764, Xu, filed Jan. 25, 2005.
U.S. Appl. No. 60/665,097, Xu, filed Mar. 24, 2005.
U.S. Appl. No. 60/665,451, Xu, filed Mar. 24, 2005.

Adams et al., "Genes duplicated by polyploidy show unequal contributions to the transcriptome and organ-specific reciprocal silencing," *PNAS*, 100(8):4649-4654 (2003).
Allen et al., "RNAi-mediated replacement of morphine with the nonnarcotic alkaloid reticuline in opium poppy," *Nature Biotechnology*, 22(12):1559-1566 (2004).
Alonso et al., "A *Hox* gene mutation that triggers nonsense-mediated RNA decay and affects alternative splicing during *Drosophila* development," *Nucleic Acids Research*, 31(14):3873-3880 (2003).
Arciga-Reyes et al., "UPF1 is required for nonsense-mediated mRNA decay (NMD) and RNAi in *Arabidopsis*" *The Plant Journal*, 47:480-489 (2006).
Arndt et al., "Colocalization of antisense RNAs and ribozymes with their target mRNAs," *Genome*, 40:785-797 (1997).
ARS-GRIN: PI 551280, "*Nicotiana tabacum*," http://www.ars-grin.gov/cgi-bin/npgs/acc/display.pl?1446216, accessed Feb. 2009).
Bak et al., "Transgenic Tobacco and *Arabidopsis* Plants Expressing the Two Multifunctional Sorghum Cytochrome P450 Enzymes, CYP79A1 and CYP71E1, Are Cyanogenic and Accumulate Metabolites Derived from Intermediates in Dhurrin Biosynthesis," *Plant Physiol.*, 123:1437-1448 (2000).
Bartoszewski et al., "Cloning of a Wound Inducible *Lycopersicon esculentum* Cytochrome P450 Gene and Lack of Regeneration of Transgenic Plants with Sense or Antisense Constructs," *J. Am. Soc. Hort. Sci.*, 127(4):535-539 (2002).
Baseggio et al., "Size and genomic location of the pMGA multigene family of *Mycoplasma gallisepticum*," *Microbiology*, 142:1429-1435 (1996).
Batard et al., "Increasing Expression of P450 and P450-Reductase Proteins from Monocots in Heterologous Systems," *Arch. Biochem. Biophys.*, 379:161-169 (2000).
Baulcombe, "Fast Forward Genetics Based on Virus-Induced Gene Silencing," *Current Opinion in Plant Biology*, 2:109-113 (1999).
Bolitho et al., "Antisense apple ACC-oxidase RNA reduces ethylene production in transgenic tomato fruit," *Plant Science*, 122:91-99 (1997).
Bosher et al., "RNA interference: genetic wand and genetic watchdog," *Nat. Cell Biol.*, 2:E31-E36 (2000).
Bosl et al., "The role of noise and positive feedback in the onset of autosomal dominant diseases," *BMC Systems Biology*, 4:1-15 (2010).
Boyette et al., "Results of year 2000 TSNA sampling program in flue-cured tobacco," *Recent Advances in Tobacco Science*, 27:17-22 (2001).
Branch, "A good antisense molecule is hard to find," *TIBS*, 23:45-50 (1998).
Brignetti et al., "Viral pathogenicity determinants are suppressors of transgene silencing in *Nicotiana benthamiana*," *EMBO J.*, 17(22):6739-6746 (1998).
Burns et al., "Large-scale analysis of gene expression, protein localization, and gene disruption in *Saccharomyces cerevisiae*," *Genes Dev.*, 8:1087-1105 (1994).
Burton et al., Changes in Chemical Composition of Burley Tobacco During Senescence and Curing. 2. Acylated Pyridine Alkaloids, American Chemical Society, pp. 579-583 (1988).
Burton et al., "Distribution of Tobacco Constituents in Tobacco Leaf Tissue. 1. Tobacco-Specific Nitrosamines, Nitrate, Nitrite, and Alkaloids," *J. Agric. Food Chem.*, 40:1050-1055 (1992).
Burton et al., "Changes in Chemical Composition of Burley Tobacco during Senescence and Curing. 2. Acylated Pyridine Alkaloids," *J .Agric. Food Chem.*, 38(3):579-584 (1998).
Bush et al., "Formation of tobacco-specific nitrosamines in air-cured tobacco," *Rec. Adv. Tob. Sci*, 27:23-46 (2001).
Byers et al., "Killing the messenger: new insights into nonsense-mediated mRNA decay" *The Journal of Clinical Investigation*, 109(1):3-6 (2002).
Byzova et al., "Transforming petals into sepaloid organs in *Arabidopsis* and oilseed rape: implementation of the hairpin RNA-mediated gene silencing technology in an organ-specific manner," *Planta*, 218:379-387 (2004).
Callis et al., "Introns increase gene expression in cultured maize cells," *Genes and Dev.*, 1:1183-1200 (1987).
Carron et al., "Genetic modification of condensed tannin biosynthesis in *Lotus corniculatus*. 1. Heterologous antisense

(56) References Cited

OTHER PUBLICATIONS dihydroflavonol reductase down-regulates tannin accumulation in "hairy root" cultures," *Theoretical and Applied Genetics*, 87(8): 1006-1015 (1994).

Caruthers, "Chapter 1: New Methods for Chemically Synthesizing Deoxyoligonucleotides," Methods of DNA and RNA Sequencing, Weissman (ed.), Praeger Publishers, New York, pp. 1-22 (1983).

Chai et al., "Reducing the maize amylopectin content through RNA interference manipulation," *Zhi Wu Sheng Li Yu Fen Zi Sheng Wu Xue Xue Buo*, 31:625-630 (2005) (English Abstract only).

Chakrabarti et al., "Inactivation of the cytochrome P450 gene CYP82E2 by degenerative mutations was a key event in the evolution of the alkaloid profile of modern tobacco," *New Phytologist*, 175:565-574 (2007).

Chakrabarti et al., "CYP82E4-mediated nicotine to nornicotine conversion in tobacco is regulated by a senescence-specific signaling pathway," *Plant Mol. Biol.*, 66: 415-427 (2008).

Chang et al., "Predicting and Testing Physical Locations of Genetically Mapped Loci on Tomato Pachytene Chromosome," *Genetics*, 176:2131-2138 (2007).

Chao et al., "A silent mutation induces exon skipping in the phenylalanine hydroxylase gene in phenylketonuria," *Hum. Genet.*, 108:14-19 (2001).

Chappell, "Biochemistry and Molecular Biology of the Isoprenoid Biosynthetic Pathway in Plants," *Annu. Rev. Plant Physiol. Plant Mol. Biol.*, 46:521-547 (1995).

Chapple, "Molecular-Genetic Analysis of Plant Cytochrome P450-Dependent Monooxygenases," *Annu. Rev. Plant Physiol. Plant Mol. Biol.*, 49:311-343 (1998).

Chelvarajan et al., "Study of Nicotine Demethylation in *Nicotiana otophora*," *J. Agric. Food Chem.*, 41:858-862 (1993).

Cheung et al., "A Floral Transmitting Tissue-Specific Glycoprotein Attracts Pollen Tubes and Stimulates Their Growth," Cell, 82:383-393 (1995).

Chintapakorn, et al., "Antisense-Mediated Down-Regulation of Putrescine N-Methyltransferase Activity in Transgenic *Nicotiana tabacum* L. can Lead to Elevated Levels of Anatabine at the Expense of Nicotine," *Plant Molecular Biology*, 53:87-105 (2003).

Cho et al., "Transcriptome Analysis and Physical Mapping of Barley Genes in Wheat-Barley Chromosome Addition Lincs," *Genetics*, 172:1277-1285 (2006).

Chou et al., "Chromosome Rearrangements in *Arabidopsis thaliana* Generated Through Cre-lox Site Specific Recombination," Plant and Animal Genome VII Conference, Abstract No. P133, 1 page (1999).

Chuang et al., "Specific and heritable genetic interference by double-stranded RNA in *Arabidopsis thaliana*," *PNAS*, 97(9):4985-4990 (2000).

Cogoni et al., "Post-transcriptional gene silencing across kingdoms," *Curr. Opin. Genet. Dev.*, 10:638-643 (2000).

Colbert et al., "High-throughput screening for induced point mutations," *Plant Physiology*, 126:480-484 (2001).

Collier et al., "A Method for Specific Amplification and PCR Sequencing of Individual Members of Multigene Families: Application to the Study of Steroid 21-Hydroxylase Deficiency," *PCR Methods and Applications*, 1:181-186 (1992).

Colliver et al., "Differential modification of flavonoid and isoflavonoid biosynthesis with an antisense chalcone synthase construct in transgenic *Lotus corniculatus*," *Plant Mol. Biol.*, 35(4):509-522 (1997).

Crookshanks et al., "The potato tuber transcriptome: analysis of 6077 expressed sequence tags," *FEBS Lett.*, 506:123-126 (2001).

Davuluri et al., "Fruit-specific RNAi-mediated suppression of DET1 enhances carotenoid and favonoid content in tomatoes," *Nat. Biotechnol.*, 23:890-895 (2005).

Dekeyser et al., "Transient Gene Expression in Intact and Organized Rice Tissues," *Plant Cell*, 2:591-602 (1990).

Dewey et al., Meeting Abstract dated Sep. 27, 2005, 1 page.

Dewey et al., Power point presentation titled "Functional characterization of the nicotine N-Demethylase gene of tobacco," Philip Morris USA, 21 pages, 2006.

Donato et al., "Fluorescence-Based Assays in Intact Cells Expressing Individual Activities for Screening Nine Cytochrome P450 (P450) Human P450 Enzymes," *Drug Metab. Dispos.*, 32(7):699-706 (2004).

D'Souza et al., "Missense and silent tau gene mutations cause frontotemporal dementia with parkinsonism-chromosome 17 type, by affecting multiple alternative RNA splicing regulatory elements" *PNAS*, 96:5598-5603 (1999).

EBI Accession AV557806, dated Jun. 16, 2000, 2 pages.

Einset, "Differential expression of antisense in regenerated tobacco plants transformed with an antisense version of a tomato ACC oxidase gene," *Plant Cell Tissue and Organ Culture*, 46(2): 137-141 (1996).

Elkind et al., "Abnormal plant development and down-regulation of phenylpropanoid biosynthesis in transgenic tobacco containing a heterologous phenylalanine ammonia-lyase gene," *PNAS*, 87(22):9057-61 (1990).

EMBL Database Report for Accession No. EU182719, Dec. 2, 2007 (XP002511576).

Escobar et al., "RNAi-mediated oncogene silencing confers resistance to crown gall tumorigenesis," *PNAS*, 98:13437-13442 (2001).

European Search Report completed on Feb. 10, 2010, in European Application No. EP 07 86 5628, 4 pages.

European Search Report completed on Mar. 31, 2011, in European Application No. EP 10 01 5540, 8 pages.

Falcon-Perez et al., "Functional Domain Analysis of the Yeast ABC Transporter Yeflp by Site-directed Mutagenesis," *J. Biol. Chem.*, 274(33):23584-23590 (1999).

Fang et al., "Multiple cis regulatory elements for maximal expression of the cauliflower mosaic virus 35S promoter in transgenic plants," *Plant Cell*, 1:141-150 (1989).

Fannin et al., "Nicotine demethylation in *Nicotiana*," *Med. Sci. Res.*, 20:807-808 (1992).

Faske et al., "Transgenic Tobacco Plants Expressing Pea Chloroplast Nmdh cDNA in Sense and Antisense Orientation," *Plant Physiol*, 115 (2): 705-715 (1997).

Fedoroff et al., "Cloning of the bronze locus in maize by a simple and generalizable procedure using the transposable controlling element Activator (Ac)," *PNAS*, 81:3825-3829 (1984).

Fire et al., "Potent and specific genetic interference by double-stranded RNA in *Caenorhabditis elegans*," *Nature*, 391:806-811 (1998).

Force et al., "Preservation of Duplicate Genes by Complementary, Degenerative Mutations," *Genetics*, 151:1531-1545 (1999).

Forsthoefel et al., "T-DNA Insertion Mutagenesis in *Arabidopsis*: Prospects and Perspectives," *Aust. J. Plant Physiol.*, 19:353-366 (1992).

Frank et al., "Cloning of Wound-Induced Cytochrome P450 Monooxygenases Expressed in Pea," *Plant Physiol.*, 110:1035-1046 (1996).

Freeman et al., "Quantitative RT-PCR: Pitfalls and Potential," *BioTechniques*, 26:112-125 (1999).

Fromm et al., "An octopine synthase enhancer element directs tissue-specific expression and binds ASF-1, a factor from tobacco nuclear extracts," *Plant Cell*, 1:977-984 (1989).

Gavilano, "Isolation, Cloning and Characterization of Novel Tobacco Cytochrome P450 Genes Involved in Secondary Metabolism," Plant Biology Meeting, American Society of Plant Biologists, Abstract No. 992, 1 page (2004).

Gavilano et al. "Genetic Engineering of *Nicotiana tabacum* for Reduced Nornicotine Content" *J. Agric. Food Chem.*, 54:9071-9078 (2006).

Gavilano et al., "Functional Analysis of Nicotine Demethylase Genes Reveals Insights into the Evolution of Modern Tobacco," *J. Biol. Chem.*, 282:249-256 (2007).

Gavilano et al., "Isolation and Characterization of the Cytochrome P450 Gene CYP82E5v2 that Mediates Nicotine to Nornicotine Conversion in the Green Leaves of Tobacco," *Plant Cell Physiol.*, 48(11):1567-1574 (2007).

GenBank Accession No. CAA64635, dated Sep. 12, 1996, 2 pages.
GenBank Accession No. BAA35080, dated Sep. 26, 2000, 2 pages.
GenBank Accession No. AAK62347, dated Jun. 14, 2001, 2 pages.
GenBank Accession No. AAK62343, dated Feb. 11, 2002, 2 pages.

(56) References Cited

OTHER PUBLICATIONS

GenBank Accession No. AAK62346, dated Feb. 11, 2002, 2 pages.
GenBank Accession No. AEK08729 dated Feb. 23, 2005, 2 pages.
GenBank Accession No. AAK62342, Sep. 20, 2005, 2 pages.
GenBank Accession No. ABA07804, dated Oct. 13, 2005, 2 pages.
GenBank Accession No. ABA07805, dated Oct. 13, 2005, 2 pages.
GenBank Accession No. ABA07807, dated Oct. 13, 2005, 2 pages.
GenBank Accession No. DQ131885, dated Oct. 13, 2005, 2 pages.
GenBank Accession No. DQ131886, dated Oct. 13, 2005, 2 pages.
GenBank Accession No. DQ131888, dated Oct. 13, 2005, 2 pages.
GenBank Accession No. DQ219341, dated Oct. 1, 2006, 2 pages.
GenBank Accession No. DQ219342, dated Oct. 1, 2006, 2 pages.
GenBank Accession No. DQ219343, dated Oct. 1, 2006, 2 pages.
GenBank Accession No. DQ219344, dated Oct. 1, 2006, 2 pages.
GenBank Accession No. DQ219345, dated Oct. 1, 2006, 2 pages.
GenBank Accession No. DQ219346, dated Oct. 1, 2006, 2 pages.
GenBank Accession No. DQ219347, dated Oct. 1, 2006, 2 pages.
GenBank Accession No. DQ219348, dated Oct. 1, 2006, 2 pages.
GenBank Accession No. DQ219349, dated Oct. 1, 2006, 2 pages.
GenBank Accession No. DQ219350, dated Oct. 1, 2006, 2 pages.
GenBank Accession No. DQ219351, dated Oct. 1, 2006, 2 pages.
GenBank Accession No. DQ219352, dated Oct. 1, 2006, 2 pages.
GenBank Accession No. DQ350312, dated Dec. 31, 2006, 2 pages.
GenBank Accession No. DQ350313, dated Dec. 31, 2006, 2 pages.
GenBank Accession No. DQ350314, dated Dec. 31, 2006, 2 pages.
GenBank Accession No. DQ350315, dated Dec. 31, 2006, 2 pages.
GenBank Accession No. DQ350316, dated Dec. 31, 2006, 2 pages.
GenBank Accession No. DQ350317, dated Dec. 31, 2006, 2 pages.
GenBank Accession No. DQ350318, dated Dec. 31, 2006, 2 pages.
GenBank Accession No. DQ350319, dated Dec. 31, 2006, 2 pages.
GenBank Accession No. DQ350320, dated Dec. 31, 2006, 2 pages.
GenBank Accession No. DQ350321, dated Dec. 31, 2006, 2 pages.
GenBank Accession No. DQ350322, dated Dec. 31, 2006, 2 pages.
GenBank Accession No. DQ350323, dated Dec. 31, 2006, 2 pages.
GenBank Accession No. DQ350324, dated Dec. 31, 2006, 2 pages.
GenBank Accession No. DQ350325, dated Dec. 31, 2006, 2 pages.
GenBank Accession No. DQ350326, dated Dec. 31, 2006, 2 pages.
GenBank Accession No. DQ350327, dated Dec. 31, 2006, 2 pages.
GenBank Accession No. DQ350328, dated Dec. 31, 2006, 2 pages.
GenBank Accession No. DQ350329, dated Dec. 31, 2006, 2 pages.
GenBank Accession No. DQ350330, dated Dec. 31, 2006, 2 pages.
GenBank Accession No. DQ350331, dated Dec. 31, 2006, 2 pages.
GenBank Accession No. DQ350332, dated Dec. 31, 2006, 2 pages.
GenBank Accession No. DQ350333, dated Dec. 31, 2006, 2 pages.
GenBank Accession No. DQ350334, dated Dec. 31, 2006, 2 pages.
GenBank Accession No. DQ350335, dated Dec. 31, 2006, 2 pages.
GenBank Accession No. DQ350336, dated Dec. 31, 2006, 2 pages.
GenBank Accession No. DQ350337, dated Dec. 31, 2006, 2 pages.
GenBank Accession No. DQ350338, dated Dec. 31, 2006, 2 pages.
GenBank Accession No. DQ350339, dated Dec. 31, 2006, 2 pages.
GenBank Accession No. DQ350340, dated Dec. 31, 2006, 2 pages.
GenBank Accession No. DQ350341, dated Dec. 31, 2006, 2 pages.
GenBank Accession No. DQ350342, dated Dec. 31, 2006, 2 pages.
GenBank Accession No. DQ350343, dated Dec. 31, 2006, 2 pages.
GenBank Accession No. DQ350344, dated Dec. 31, 2006, 2 pages.
GenBank Accession No. DQ350345, dated Dec. 31, 2006, 2 pages.
GenBank Accession No. DQ350346, dated Dec. 31, 2006, 2 pages.
GenBank Accession No. DQ350347, dated Dec. 31, 2006, 2 pages.
GenBank Accession No. DQ350348, dated Dec. 31, 2006, 2 pages.
GenBank Accession No. DQ350349, dated Dec. 31, 2006, 2 pages.
GenBank Accession No. DQ350350, dated Dec. 31, 2006, 2 pages.
GenBank Accession No. DQ350351, dated Dec. 31, 2006, 2 pages.
GenBank Accession No. DQ350352, dated Dec. 31, 2006, 2 pages.
GenBank Accession No. DQ350353, dated Dec. 31, 2006, 2 pages.
GenBank Accession No. DQ350354, dated Dec. 31, 2006, 2 pages.
GenBank Accession No. DQ350355, dated Dec. 31, 2006, 2 pages.
GenBank Accession No. DQ350356, dated Dec. 31, 2006, 2 pages.
GenBank Accession No. DQ350357, dated Dec. 31, 2006, 2 pages.
GenBank Accession No. DQ350358, dated Dec. 31, 2006, 2 pages.
GenBank Accession No. DQ350359, dated Dec. 31, 2006, 2 pages.
GenBank Accession No. DQ350360, dated Dec. 31, 2006, 2 pages.
GenBank Accession No. DQ350361, dated Dec. 31, 2006, 2 pages.
GenBank Accession No. DQ350362, dated Dec. 31, 2006, 2 pages.
GenBank Accession No. DQ350363, dated Dec. 31, 2006, 2 pages.
GenBank Accession No. DQ205656, dated Jan. 18, 2007, 2 pages.
GenBank Accession No. ABA07806, dated Mar. 7, 2007, 2 pages.
GenBank Accession No. DQ131887, dated Mar. 7, 2007, 2 pages.
Ghosh, "Polyamines and plant alkaloids," *Indian J. Exp. Biol.*, 38:1086-1091 (2000).
Goldrick et al., "Molecular Genetic Analysis of the User Group Associated with Two Mouse Light Chain Genetic Markers," *J. Exp. Med.*, 162:713-728 (1985).
Graham-Lorence et al., "P450s: Structural similarities and functional differences," *FASEB J.*, 10:206-214 (1996).
Guo et al., "Protein Tolerance to Random Amino Acid Change," *PNAS*, 101(25):9205-9210 (2004).
Hao et al., "Mechanism of Nicotine N-Demethylation in Tobacco Cell Suspension Cultures," *Phytochemistry*, 41(2):477-482 (1995).
Hao et al., "Nicotine N-Demethylase in Cell-Free Preparations from Tobacco Cell Cultures," *Phytochemistry*, 42(2):325-329 (1996).
Hao et al., "Evidence in Favour of an Oxidative N-Demethylation of Nicotine to Nornicotine in Tobacco Cell Cultures," *Journal Plant Physiology*, 152:420-426 (1998).
Haseloff et al., "Simple RNA enzymes with new and highly specific endoribonuclease activities," *Nature*, 334:585-591 (1998).
Hayes et al., "Blotting techniques for the study of DNA, RNA, and proteins," *BMJ*, 299(14):965-968 (1989).
Hecht et al., "The relevance of tobacco-specific nitrosamines to human cancer," *Cancer Surveys*, 8(2):273-294 (1989).
Hecht, "Biochemistry, Biology, and Carcinogenicity of Tobacco-Specific N-Nitrosamines," *Chemical Research in Toxicology*, 11(6):559-603 (1998).
Helene et al., "Control of Gene Expression by Triple Helix-Forming Oligonucleotides," *Ann. N.Y. Acad. Sci.*, 660:27-36 (1992).
Helene, "The anti-gene strategy: control of gene expression by triplex-forming-oligonucleotides," *Anti-Cancer Drug Des.*, 6:569-584 (1991).
Helliwell et al., "High-throughput vectors for efficient gene silencing in plants," *Funct. Plant Biol.*, 29:1217-1225 (2002).
Henikoff et al., "Single-Nucleotide Mutations for Plant Functional Genomics," *Annu. Rev. Plant Biol.*, 54:375-401 (2003).
Herbik et al., "Isolation, characterization and cDNA cloning of nicotianamine synthase from barley," *Eur J Biochem*, 265(1): 231-9 (1999).
Hibino et al., "Increase of Cinnamaldehyde Groups in Lignin of Transgenic Tobacco Plants Carrying an Antisense Gene for Cinnamyl Alcohol Dehydrogenase," *Biosci. Biotec. Biochem*, 59:929-931 (1995).
Hildering et al., "Chimeric Structure of the Tomato Plant After Seed Treatment with EMS and X-Rays," The Use of Induced Mutations in Plant Breeding, Pergamon Press, pp. 317-320 (1965).
Hill et al., "Functional analysis of conserved histidines in ADP-glucose pyrophosphorylase from *Escerichia coli*," *Biochem. Biophys. Res. Commun.*, 244:573-577 (1998) (Abstract only).
Hoekema et al., "A binary plant vector strategy based on separation of the vir- and T-region of the *Agrobacterium tumefaciens* Ti-plasmid," *Nature*, 303:179-180 (1983).
Hoffmann et al., "Tobacco-specific N-nitrosamines and Areca-derived N-nitrosamines: chemistry, biochemistry, carcinogenicity, and relevance to humans," *Journal of Toxicology and Environmental Health*, 41:1-52 (1994).
Huang et al., "Insights into Regulation and Function of the Major Stress-Induced hsp70 Molecular Chaperone In Vivo: Analysis of Mice with Targeted Gene Disruption of the hsp70.1 or hsp70.3 Gene," *Mol Cell Biol*, 21(24):8575-8591 (2001).
Ingelbrecht et al., "Posttranscriptional silencing of reporter transgenes in tobacco correlates with DNA methylation," *PNAS*, 91:10502-10506 (1994).
International Preliminary Report on Patentability in PCT/US07/087386 mailed Jun. 25, 2009, 6 pages.

(56) References Cited

OTHER PUBLICATIONS

International Search Report and the Written Opinion of the International Searching Authority, or the Declaration mailed on May 4, 2012, in International Application No. PCT/US2012/026864 (13 pages).
International Search Report and the Written Opinion of the International Searching Authority, or the Declaration mailed on Jul. 4, 2012, in International Application No. PCT/US2012/026795 (15 pages).
Isshiki et al., "Nonsense-mediated decay of mutant waxy mRNA in rice," *Plant Physiology*, 125:1388-1395 (2001).
Jack et al., "Relative stability of nicotine to nornicotine conversion in three burley cultivars," Coresta Congress, Kyoto, Agro-Phyto groups, Abstract AP2 (2004).
Johnston et al., "Dosage-sensitive function of retinoblastoma related and convergent epigenetic control are required during the *Arabidopsis* life cycle," *PLoS Genet*, 6(6):e1000988 (2010).
Jorgensen et al., "Chalcone synthase cosuppression phenotypes in petunia flowers: comparison of sense vs. antisense constructs and single-copy vs. complex T-DNA sequences," *Plant Mol. Biol.*, 31:957-973 (1996).
Julio et al. "Reducing the content of nornicotine in tobacco via targeted mutation breeding," *Mol. Breeding*, 21:369-381 (2008).
Julio et al., "Targeted Mutation Breeding as a tool for tobacco crop improvement," presentation made in Oct. 2008.
Kafri et al., "The regulatory utilization of genetic redundancy through responsive backup circuits," *PNAS*, 103(31):11653-11658 (2006).
Kempin et al., "Targeted disruption in *Arabidopsis*," *Nature*, 389:802-803 (1997).
Keskin et al., "A new, structurally nonredundant, diverse data set of protein-protein interfaces and its implications," *Protein Science*, 13:1043-1055 (2004).
Kim et al., "*Arabidopsis* CYP85A2, a Cytochrome P450, Mediates the Baeyer-Villiger Oxidation of Castasterone to Brassinolide in Brassinosteroid Biosynthesis," *Plant Cell*, 17:2397-2412 (2005).
Klahre et al., "High molecular weight RNAs and small interfering RNAs induce systemic posttranscriptional gene silencing in plants," *PNAS*, 99:11981-11986 (2002).
Klink et al., "The Efficacy of RNAi in the Study of the Plant Cytoskeleton," *J. Plant Growth Regul.*, 19:371-384 (2000).
Koornneef, "Chapter 1: Classical mutagenesis in higher plants," *Molecular Plant Biology*, Gilmartin and Bowler, ed., Oxford University Press, pp. 1-11 (2002).
Koshinsky et al., "Cre-lox site-specific recombination between *Arabidopsis* and tobacco chromosomes," *Plant J.*, 23(6):715-722 (2000).
Kusaba et al., "Low glutelin content1: A Dominant Mutation That Suppresses the Glutelin Multigene Family via RNA Silencing in Rice," *Plant Cell*, 15:1455-1467 (2003).
Kynast et al., "Dissecting the maize genome by using chromosome addition and radiation hybrid lines," *PNAS*, 101(26):9921-9926 (2004).
Lazar et al., "Transforming Growth Factor α Mutation of Aspartic Acid 47 and Leucine 48 Results in Different Biological Activities," *Mol. Cell. Biol.*, 8(3):1247-1252 (1988).
Levin et al., "Methods of double-stranded RNA-mediated gene inactivation in *Arabidopsis* and their use to define an essential gene in methionine biosynthesis," *Plant Mol. Biol.*, 44:759-775 (2000).
Lewis et al., "Three nicotine demethylase genes mediate nornicotine biosynthesis in *Nicotiana tabacum* L.: Functional characterization of the CYP82E10 gene, "*Phytochemistry*, 71:1988-1998 (2010).
Lewis, et al. "RNA interference (RNAi)-induced suppression of nicotine demethylase activity reduces levels of a key carcinogen in cured tobacco leaves." *Plant Biotechnology Journal*, 6:1-9 (2008).
Liu et al., "High-Stearic and High-Oleic Cottonseed Oils Produced by Hairpin RNA-Mediated Post-Transcriptional Gene Silencing," *Plant Physiol.*, 129:1732-1743 (2002).
Liu et al., "Identification and characterization of HTD2: a novel gene negatively regulating tiller bud outgrowth in rice," *Planta*, 230(4):649-658 (2009).

Liu et al "Genetic and transformation studies reveal negative regulation of ERS1 ethylene receptor signaling in *Arabidopsis*," *BMC Plant Biol*, 10 :60-73 (2010).
Maher, "DNA Triple-Helix Formation: An Approach to Artificial Gene Repressors?" *BioEssays*, 14(12):807-815 (1992).
Maniatis et al., "Regulation of inducible and tissue-specific gene expression," *Science*, 236:1237-1245 (1987).
Mansoor et al. "Engineering novel traits in plants through RNA interference," *Trends in Plant Science*, 11(11):1-7 (2006).
Maquat, "Nonsense-mediated mRNA decay," *Curr. Biol.*, 12(6):R196-R197 (2002).
Matthew, "RNAi for plant functional genomics," *Comparative and Functional Genomics*, 5:240-244 (2004).
McDougall et al., "Detection of Viral DNA and RNA by In Situ Hybridization," *J. Histochem. Cytochem.*, 34:33-38 (1986).
McKinney et al., "Sequence-based identification of T-DNA insertion mutations in *Arabidopsis*: actin mutants act2-1 and act4-1," *Plant J.*, 8(4):613-622 (1995).
Mesnard et al., "Evidence for the involvement of tetrahydrofolate in the demethylation of nicotine by *Nicotiana plumbaginifolia* cell-suspension cultures," *Planta*, 214:911-919 (2002).
Mette et al., "Transcriptional silencing and promoter methylation triggered by double-stranded RNA," *EMBO J.*, 19(19):5194-5201 (2000).
Mol et al., "Regulation of plant gene expression by antisense RNA," *FEBS Lett.*, 268(2):427-430 (1990).
Napoli et al., "Introduction of a Chimeric Chalcone Synthase Gene into Petunia Results in Reversible Co-Suppression of Homologous Genes in trans," *Plant Cell*, 2:279-289 (1990).
Nawrath et al., "Salicylic Acid Induction-Deficient Mutants of *Arabidopsis* Express PR-2 and PR-5 and Accumulate High Levels of Camalexin after Pathogen Inoculation," *Plant Cell*, 11:1393-1404 (1999).
Needleman et al., "A General Method Applicable to the Search for Similarities in the Amino Acid Sequence of Two Proteins," *J. Mol. Biol.*, 48:443-453 (1970).
Nelson et al., "Comparative Genomics of Rice and *Arabidopsis*. Analysis of 727 Cytochrome P450 Genes and Pseudogenes from a Monocot and a Dicot," *Plant Physiol.*, 135:756-772 (2004).
Nelson et al., "Comparison of cytochrome P450 (*CYP*) genes from the mouse and human genomes, including nomenclature recommendations for genes, pseudogenes and alternative-splice variants," *Pharmacogenetics*, 14:1-18 (2004).
Ng et al., "Specific Detection and Confirmation of *Campylobacter jejuni* by DNA Hybridization and PCR," *Appl. Environ. Microbiol.*, 63(11):4558-4563 (1997).
Nishihara et al., "Flavanoid components and flower color change in transgenic tobacco plants by suppression of chalcone isomerase gene," *FEBS Lett.*, 579:6074-6078 (2005).
Odell et al., "Identification of DNA sequences required for activity of the cauliflower mosaic virus 35S promoter," *Nature*, 313:810-812 (1985).
Office Action mailed on Oct. 18, 2006, in U.S. Appl. No. 10/293,252.
Office Action mailed on Oct. 30, 2006, in U.S. Appl. No. 10/686,947.
Office Action mailed on Nov. 14, 2006, in U.S. Appl. No. 10/387,346.
Office Action mailed on Nov. 14, 2006, in U.S. Appl. No. 10/340,861.
Office Action mailed on May 4, 2007, in U.S. Appl. No. 10/943,507.
Office Action mailed on Jun. 12, 2007, in U.S. Appl. No. 10/934,944.
Ogita et al., "Application of RNAi to confirm theobromine as the major intermediate for caffeine biosynthesis in coffee plants with potential for construction of decaffeinated varieties," *Plant Mol. Biol.*, 54:931-941 (2004).
Ohshima et al., "Nucleotide sequence of the PR-1 gene of *Nicotiana tabacum*," *FEBS Letters*, 225:243-246 (1987).
Oliver et al , "Inhibition of tobacco NADH-hydroxypyruvate reductase by expression of a heterologous antisense RNA derived from a cucumber cDNA: Implications for the mechanism of action of antisense RNAs," *Mol Gen Genet*, 239(3):425-34 (1993).
Pearson et al., "Improved tools for biological sequence comparison," *PNAS*, 85:2444-2448 (1988).
Peele et al., "Formation of Tobacco-specific Nitrosamines in Flue-cured Tobacco," CORESTA Meeting, Agro-Phyto Groups, Suzhou, China (1999).

(56) References Cited

OTHER PUBLICATIONS

Pickett et al., "Seeing Double: Appreciating Genetic Redundancy," *Plant Cell*, 7:1347-1356 (1995).
Plant Variety Protection Office (USDA-AMS, Beltsville, MD, http://www.ars-grin.gov/cgi-bin/npgs/htmllpvp.pl?Tobbaco, accessed Feb. 2009).
Puchta et al., "Two different but related mechanisms are used in plants for the repair of genomic double-strand breaks by homologous recombination," *PNAS*, 93:5055-5060 (1996).
Qin et al., "Cre recombinase-mediated site-specific recombination between plant chromosomes," *PNAS*, 91:1706-1710 (1994).
Qiu et al. "A computational study of off-target effects of RNA interference." *Nucleic Acids Research*, 33(6)1834-1847 (2005).
Ralston et al., "Cloning, Heterologous Aristolochene-1,3-Dihydroxylase from Expression, and Functional Characterization of 5-epi-Tobacco (*Nicotiana tabacum*)," *Arch. Biochem. Biophys.*, 393(2):222-235 (2001).
Reid et al., "Studies on the Fermentation of Tobacco 1. The Microflora of Cured and Fermenting Cigar-leaf Tobacco," Bulletin 356, Pennsylvania Agricultural Experiment Station, State College, PA, 18 pages (1938).
Rodermel et al., "Nuclear-Organelle Interactions: Nuclear Antisense Gene Inhibits Ribulose Biphosphate Carboxylase Enzyme Levels in Transformed Tobacco Plants," *Cell*, 55:673-681(1988).
Rohr et al., "Tandem inverted repeat system for selection of effective transgenic RNAi strains of *Chlamydomonas*," *Plant J.*, 40:611-621 (2004).
Salehuzzaman et al., "Isolation and characterization of a cDNA encoding granule-bound starch synthase in cassava (*Manihot esculenta* Crantz) and its antisense expression in potato," *Plant Mol Biol*, 23 (5):947-62 (1993).
Schenk et al., "Coordinated plant defense responses in *Arabidopsis* revealed by microarray analysis," *PNAS*, 97(21):11655-11660 (2000).
Schnable et al., "Genetic recombination in plants," *Curr. Opin. Plant Biol*, 1:123-129 (1998).
Schopfer et al., "Identification of elicitor-induced cytochrome P450s of soybean (*Glycine max* L.) using differential display of mRNA," *Mol. Gen. Genet.*, 258:315-322 (1998).
Seal et al., "Isolation of a Pseudomonas solanacearum-Specific DNA Probe by Subtraction Hybridization and Construction of Species-Specific Oligonucleotide Primers for Sensitive Detection by the Polymerase Chain Reaction," *Appl. Environ. Microbiol.*, 58(2):3751-3758 (1992).
Sequence 6912f1 obtained from the Internet at http://mrg.pscsiken.go.ip/nicotiana/menu/069.html on Dec. 6, 2007, 1 page.
Shah et al., "Expression of Silent Mutations in Disease Phenotype," Abstract for presentation at 11th International Congress of Human Genetics, 1 page, (2006).
Shen et al., "Resistance Gene Candidates identified by PCR with Degenerate Oligonucleotide Primers Map to Clusters of Resistance Genes in Lettuce," *Molecular Plant-Microbe Interactions*, 11(8):815-823 (1998).
Shew et al. (Eds.), "Compendium of Tobacco Diseases," published by American Phytopathology Society, 99 pages. (1991).
Siminszky et al., "Conversion of nicotine to nornicotine in *Nicotiana tabacum* is mediated by CYP82E4, a cytochrome P450 monooxygenase," *PNAS*, 102(41):14919-14924 (2005).
Sinvany-Villalobo et al., "Expression in Multigene Families. Analysis of Chloroplast and Mitochondrial Proteases," *Plant Physiol*, 135:1336-1345 (2004).
Skarnes, "Entrapment Vectors: A New Tool for Mammalian Genetics," *Bio/Technology*, 8:827-831 (1990).
Smith et al., "Comparison of Biosequences," *Adv. Appl. Math.*, 2:482-489 (1981).
Smith et al., "Total silencing by intron-spliced hairpin RNAs," *Nature*, 407:319-320 (2000).
Spradling et al., "Gene disruptions using P transposable elements: An integral component of the *Drosophila* genome project," *PNAS*, 92:10824-10830 (1995).
Stalberg et al., "Deletion analysis of a 2S seed storage protein promoter of *Brassica napus* in transgenic tobacco," *Plant Mol. Biol.*, 23:671-683 (1993).
Sundaresan et al., "Patterns of gene action in plant development revealed by enhancer trap and gene trap transposable elements," *Genes Dev.*, 9:1797-1810 (1995).
Sureka et al., "Positive Feedback and Noise Activate the Stringent Response Regulator Rel in Mycobacteria," *PLoS One*, 3(3):e1771 (2008).
Takeda et al., "Differentiation between Wild and Vaccine-Derived Strains of Poliovirus by Stringent Microplate Hybridization of PCR Products," *J. Clin. Microbiol.*, 32:202-204 (1994).
Takemoto et al., "Molecular Cloning of a Defense-Response-Related Cytochrome P450 Gene from Tobacco," *Plant Cell Physiol.*, 40(12):1232-1242 (1999).
Takken et al. "A functional cloning strategy, based on a binary PVX-expression vector, to isolate HR-inducing cDNAs of plant pathogens." *The Plant Journal*, 24(2): 275-283 (2000).
Tang et al., "Using RNAi to improve plant nutritional value: from mechanism to application," *TRENDS in Biotechnology*, 22(9):463-469 (2004).
Tavernarakis et al., "Heritable and inducible genetic interference by double-stranded RNA encoded by transgenes," *Nat. Genet.*, 24:180-183 (2000).
Temple et al., "Modulation of glutamine synthetase gene expression in tobacco by the introduction of an alfalfa glutamine synthetase gene in sense and antisense orientation: molecular and biochemical analysis," *Mol Gen Genet*, 236(2-3):315-25 (1993).
Thomas et al., "Size constraints for targeting post-transcriptional gene silencing and for RNA directed methylation in *Nicotiana benthamiana* using a potato virus X vector," *Plant J.*, 25(4):417-425 (2001).
Thornton et al., "From structure to function: Approaches and limitations," *Nature Structural Biology, Structural Genomics Supplement*, pp. 991-994 (2000).
Till et al., "Discovery of induced point mutations in maize genes by TILLING," *BMC Plant Biology*, 4:12 (2004).
Toscano et al., "A silent mutation (2939G>A, exon 6; CYP2D6*59) leading to impaired expression and function of CYP2D6," *Pharmacogenet. Genomics*, 16(10):767-770 (2006).
Travella, et al. "RNA Interference-Based Gene Silencing as an Efficient Tool for Functional Genomics in Hexaploid Bread Wheat." *Plant Physiology*, 142:6-20 (2006).
Trevanion et al., "NADP-Malate Dehydrogenase in the C4 Plant *Flaveria bidentis*," *Plant Physiol*, 113(4):1153-1165 (1997).
Turner et al., "Post-transcriptional gene-silencing and RNA interference: genetic immunity, mechanisms and applications," *J. Chem. Technol. Biotechnol.*, 75:869-882 (2000).
United States, "Tobacco in the United States," Miscellaneous Publication No. 867, U.S. Dept. of Agriculture, Agricultural Marketing Service, 27 pages (1979).
Vaistij et al., "Spreading of RNA Targeting and DNA Methylation in RNA Silencing Requires Transcription of the Target Gene and a Putative RNA-Dependent RNA Polymerase," *Plant Cell*, 14:857-867 (2002).
Van der Krol et al., "An anti-sense chalcone synthase gene in transgenic plants inhibits flower pigmentation," *Nature*, 333:866-869 (1988).
Van der Krol et al., "Antisense genes in plants: an overview," *Gene*, 72:45-50 (1988).
Vaucheret et al., "Post-transcriptional gene silencing in plants," *J. Cell Sci.*, 114:3083-3091 (2001).
Veena et al., "Glyoxalase I from *Brassica juncea*: molecular cloning, regulation and its overexpression confer tolerance in transgenic tobacco under stress," *Plant Journal*, 17(4):385-395 (1999).
Verdaguer et al., "Functional organization of the cassava vein mosaic virus (CsVMV) promoter," *Plant Mol. Biol.*, 37(6):1055-1067 (1998).
Verkerk, "Chimerism of the tomato plant after seed irradiation with fast neutrons," *Neth. J. Agric. Sci.*, 19:197-203 (1971).
Voss et al., "The role of enhancers in the regulation of cell-type-specific transcriptional control," *Trends Biochem. Sci.*, 11(7):287-289 (1986).

(56) References Cited

OTHER PUBLICATIONS

Wang et al., "Suppression of a P450 hydroxylase gene in plant trichome glands enhances natural product-based aphid resistance," *Nat. Biotechnol.*, 19:371-374 (2001).
Wang et al., "Isolation and characterization of the CYP71D16 trichome-specific promoter from *Nicotania tabacum* L," *J. Exp. Botany*, 53(376):1891-1897 (2002).
Wang et al., "Elucidation of the functions of genes central to diterpene metabolism in tobacco trichomes using posttranscriptional gene silencing," *Planta*, 216:686-691 (2003).
Waterhouse et al., "Virus resistance and gene silencing in plants can be induced by simultaneous expression of sense and antisense RNA," *PNAS*, 95:13959-13964 (1998).
Weigel et al., "A developmental switch sufficient for flower initiation in diverse plants," *Nature*, 377:495-500 (1995).
Weising et al., "Foreign Genes in Plants: Transfer, Structure, Expression, and Applications," *Ann. Rev. Genetics*, 22:421-477 (1988).
Werck-Reichhart et al., "Cytochromes P450: a success story," *Genome Biology*, 1(6):reviews3003.1-3003.9 (2000).
Werck-Reichhart et al., "Cytochromes P450," The *Arabidopsis* Book, American Society of Plant Biologists, 28 pages (2002).
Wernsman et al., "Time and site of nicotine conversion in tobacco," *Tobacco Science*, 167(22):226-228 (1968).
Wernsman et al., "Relative Stability of Alleles at the Nicotine Conversion Locus of Tobacco," *Tobacco Science*, 14:34-36 (1970).
Wernsman et al., "Chapter Seventeen: Tobacco." *Cultivar Development. Crop Species.*, W. H. Fehr (ed.), MacMillan Publishing Go., Inc., New York, N.Y., pp. 669-698 (1987).
Wesley et al., "Construct design for efficient, effective and high-throughput gene silencing in plants," *The Plant Journal*, 27(6): 581-590 (2001).
Wetmur, "DNA Probes: Applications of the Principles of Nucleic Acid Hybridization" *Critical Reviews in Bio. and Mol. Biol.*, 26:227-259, (1991).
Whitbred et al., "Molecular Characterization of CYP73A9 and CYP82A1 P450 Genes Involved in Plant Defense in Pea," *Plant Physiol.*, 124:47-58 (2000).
Wu et al. "Herbivory Rapidly Activates MAPK Signaling in Attacked and Unattacked Leaf Regions but Not between Leaves of *Nicotiana attenuata.*" *The Plant Cell*, 19:1096-1122 (2007).
Xiong et al., "Different effects on ACC oxidase gene silencing triggered by RNA interference in transgenic tomato," *Plant Cell*, 23:639-646 (2004).
Xu et al. "Computational Estimation and Experimental Verification of Off-Target Silencing during Posttranscriptional Gene Silencing in Plants," *Plant Physiology*, 142:429-440 (2006).
Xu et al., "Biochemical and molecular characterizations of nicotine demethylase in tobacco," *Physiologia Plantarum*, 129(2):307-319 (2007).
Zwart et al., "Rapid Screening for Freshwater Bacterial Groups by Using Reverse Line Blot Hybridization," *Appl. Environ. Microbiol.*, 69(10):5875-5883 (2003).
Accession No. PI 543792 in the *Germplasm Resources Information Network (GRIN)* [online database] from www.ars-grin.gov/cgi-bin/npgs/acc/display.pl?1438728.
Horlow et al., "Transfer of Cytoplasmic Male Sterility by Spontaneous Androgenesis in Tobacco (*Nicotiana tabacum* L.)", *Euphytica*, 66:45-53 (1993).
International Preliminary Report on Patentability and Written Opinion of the International Searching Authority in International Application No. PCT/US2012/026795 mailed Sep. 3, 2013.
Bindler et al., "Report of the CORESTA Task Force Genetically Modified Tobacco: Detection Methods," *CORESTA Task Force Genetically Modified Tobacco—Detection Methods*, pp. 1-41 (1999).
Electronic Administrative Briefings, Jun. 2008, Office of the Dean, College of Agriculture & Life Sciences, NC State University, pp. 1-11, Jun. 1, 2008, *Web*, Apr. 29, 2015 < http://harvest.cals.ncsu.edu/applications/calswebsite/filelibrary/brief_0608.pdf>.
International Search Report and Written Opinion mailed Jun. 2, 2015, in International Application No. PCT/US2015/018393 (11 pgs.).
International Search Report and Written Opinion Jul. 6, 2015, in International Application No. PCT/US2015/018408 (16 pgs.)
International Preliminary Report on Patentability mailed Jul. 23, 2015, in International Application No. PCT/US2014/011035 (8 pgs.)
Reed, "Curing Information: Curing Tobacco," *2008 Flue-cured Tobacco Production Guide*, Virginia Cooperative Extension, pp. 61-64 (2008).
Saunders et al., "The Use of AFLP Techniques for DNA Fingerprinting in Plants," *Beckman Coulter*, Technical Application Information A-1910A:1-9 (2001).
Slater et al., "Chapter 2: Plant Tissue Culture," *Plant Biotechnology: The Genetic Manipulation of Plants*, Oxford University Press, pp. 37-53 (2008).
Binder et al., "Report of the CORESTA Task Force Genetically Modified Tobacco: Detection Methods," pp. 1-41.
Denduangboripant et al., "Determination of Local Tobacco Cultivars Using ISSR Molecular Marker," *Chiang Mai J. Sci.*, 37(2):293-303 (2010).
Maryan et al., "Assessing the genetic diversity of tobacco (*Nicotiana tabacum* L.) varieties," *Crop Breeding Journal*, 2(2):125-132 (2012).
Weising et al., "DNA Fingerprinting in Plants," Principles, Methods, and Applications, Second Edition, CRC Press, Florida, pp. 1-470 (2005).
Zhang et al., "Genetic diversity among flue-cured tobacco (*Nicotiana tabacum* L.) revealed by amplified fragment length polymorphism," *Botanical Studies*, 47:223-229 (2006).
International Search Report mailed on Apr. 23, 2014, in International Patent Application No. PCT/US2014/011035.
Written Opinion of the International Searching Authority mailed on Apr. 23, 2014, in International Patent Application No. PCT/US2014/011035.
Jack et al., "Relative Stability of Nicotine to Nornicotine Conversion in Three Burley Cultivars," basis for an abstract published in COREST Congress Abstract AP2, Kyoto (2004) Agro Phyto Groups.
Mann et al., "Inheritance of the Conversion of Nicotine to Nornicotine in Varieties of Nicotiana tabacum L. and Related Amphiploids," *Crop Sci.*, 4(4):349-53 (1964).
International Search Report and Written Opinion mailed on Aug. 28, 2014, in International Patent Application No. PCT/US2014/019381.
Chen et al., "Toxicological Analysis of Low-Nicotine and Nocotine-Free Cigarettes," *Toxicology*, 249:194-203 (2008).
Invitation to Pay Additional Fees issued on Jun. 23, 2014, in International Patent Application No. PCT/US2014/019381, 8 pages.
Ruiz et al., "Nicotine-free and salt-tolerant tobacco plants obtained by grafting to salinity-resistant rootstocks of tomato," *Physiologia Plantarum*, 124:465-475 (2005).

\* cited by examiner

TOBACCO INBRED PLANTS ALBEX1F AND ALBEX1MS

CROSS-REFERENCE TO RELATED APPLICATIONS

This application is a continuation-in-part of prior application Ser. No. 11/611,782, filed Dec. 15, 2006 (pending). This application claims the benefit under 35 U.S.C. §119 of U.S. Provisional Application No. 61/447,487, filed Feb. 28, 2011 and U.S. Provisional Application No. 61/507,732, filed Jul. 14, 2011, each of which provisional applications is herein incorporated by reference in its entirety, including its respective sequence listing.

INCORPORATION OF SEQUENCE LISTING

This application contains a sequence listing, which is herein incorporated by reference in its entirety. An electronic equivalent paper copy/computer-readable form of the sequence listing is submitted herewith electronically via EFS-Web and contains the file named "P33794US02_seqlist.txt", which is 16,384 bytes in size (measured in Windows XP), which was created on Feb. 23, 2012, and which is herein incorporated by reference in its entirety.

FIELD OF THE INVENTION

The present invention provides tobacco inbred plants ALBEX1F and ALBEX1MS. The present invention also provides parts of such plants and products made from those parts. The present invention also includes progeny of the provided plants including hybrids.

BACKGROUND OF THE INVENTION

Tobacco (*Nicotiana tabacum* L.) is an important commercial crop in the United States as well as in other countries. In tobacco plants, N-demethylation of nicotine results in nornicotine, a secondary alkaloid known to be a precursor for formation of N-Nitrosonornicotine ("NNN") in cured leaves. NNN is an undesired component of cured leaves.

The predominant alkaloid found in commercial tobacco varieties is nicotine, typically accounting for 90-95% of the total alkaloid pool. The remaining alkaloid fraction is comprised primarily of three additional pyridine alkaloids: nornicotine, anabasine, and anatabine. Nornicotine is generated directly from nicotine through the activity of the enzyme nicotine N-demethylase. Nornicotine usually represents less than 5% of the total pyridine alkaloid pool, but through a process termed "conversion," tobacco plants that initially produce very low amounts of nornicotine give rise to progeny that metabolically "convert" a large percentage of leaf nicotine to nornicotine. In tobacco plants that have genetically converted (termed "converters"), the great majority of nornicotine production occurs during the senescence and curing of the mature leaf (Wernsman and Matzinger (1968) *Tob. Sci.* 12:226-228). Burley tobaccos are particularly prone to genetic conversion, with rates as high as 20% per generation observed in some cultivars.

During the curing and processing of the tobacco leaf, a portion of the nornicotine is metabolized to the compound NNN, a tobacco-specific nitrosamine (TSNA) that has been asserted to be carcinogenic in laboratory animals (Hecht and Hoffmann (1990) *Cancer Surveys* 8:273-294; Hoffmann et al. (1994) *J. Toxicol. Environ. Health* 41:1-52; Hecht (1998) *Chem. Res. Toxicol.* 11:559-603). In flue-cured tobaccos, TSNAs are found to be predominantly formed through the reaction of alkaloids with the minute amounts of nitrogen oxides present in combustion gases formed by the direct-fired heating systems found in traditional curing barns (Peele and Gentry (1999) "Formation of Tobacco-specific Nitrosamines in Flue-cured Tobacco," CORESTA Meeting, Agro-Phyto Groups, Suzhou, China). Retrofitting these curing barns with heat-exchangers virtually eliminated the mixing of combustion gases with the curing air and dramatically reduced the formation of TSNAs in tobaccos cured in this manner (Boyette and Hamm (2001) *Rec. Adv. Tob, Sci.* 27:17-22.). In contrast, in the air-cured Burley tobaccos, TSNA formation proceeds primarily through reaction of tobacco alkaloids with nitrite, a process catalyzed by leaf-borne microbes (Bush et al. (2001) *Rec. Adv. Tob. Sci,* 27:23-46). Thus far, attempts to reduce TSNAs through modification of curing conditions while maintaining acceptable quality standards have not proven to be successful for the air-cured tobaccos.

SUMMARY OF THE INVENTION

In an aspect, the present invention includes a seed of tobacco cultivar ALBEX1F, a representative sample seed of the cultivar having been deposited with the ATCC under ATCC Accession No. PTA-11716 on behalf of Altria Client Services Inc. on Feb. 28, 2011.

In an aspect, the present invention includes a tobacco plant, or a part thereof, produced by growing a seed of tobacco cultivar ALBEX1F, a representative sample seed of the cultivar having been deposited with the ATCC under ATCC Accession No. PTA-11716.

In an aspect, the present invention includes a harvested leaf of a tobacco plant, or part thereof, produced by growing a seed of tobacco cultivar ALBEX1F, a representative sample seed of the cultivar having been deposited with the ATCC under ATCC Accession No. PTA-11716.

In an aspect, the present invention includes a harvested leaf of a tobacco plant, or part thereof, produced by growing a seed of tobacco cultivar ALBEX1F, a representative sample seed of the cultivar having been deposited with the ATCC under ATCC Accession No. PTA-11716, wherein said leaf has a reduced amount of nornicotine and/or N'-nitrosonornicotine (NNN) and/or more stably low nicotine conversion as compared to a leaf from TN 90 or most other commercial burley tobacco cultivars grown under similar conditions.

In an aspect, the present invention includes a harvested leaf of a tobacco plant produced by growing a seed of tobacco cultivar ALBEX1F, a representative sample seed of the cultivar having been deposited with the ATCC under ATCC Accession No. PTA-11716, wherein said leaf has a reduced amount of nornicotine and/or N'-nitrosonornicotine (NNN) and/or more stably low nicotine conversion as compared to a leaf from TN 90 or most other commercial burley tobacco cultivars grown under similar conditions, wherein the reduced amount of nornicotine and/or N'-nitrosonornicotine (NNN) is reduced in a smoke stream produced from said leaf as compared to a leaf from TN 90 or most other commercial burley tobacco cultivars grown under similar conditions.

In an aspect, the present invention includes a tobacco product, prepared from the tobacco plant, or part thereof, produced by growing a seed of tobacco cultivar ALBEX1F, a representative sample seed of the cultivar having been deposited with the ATCC under ATCC Accession No PTA-11716, wherein said product is selected from the group consisting of pipe tobacco, cigar tobacco, cigarette tobacco, chewing tobacco, leaf tobacco, shredded tobacco, and cut tobacco.

In an aspect, the present invention includes a tobacco product prepared from the tobacco plant, or part thereof, produced by growing a seed of tobacco cultivar ALBEX1F, a representative sample seed of the cultivar having been deposited with the ATCC under ATCC Accession No. PTA-11716, wherein said product is selected from the group consisting of pipe tobacco, cigar tobacco, cigarette tobacco, chewing tobacco, leaf tobacco, shredded tobacco, and cut tobacco, and wherein said product is further selected from the group consisting of a cigarillo, a non-ventilated recess filter cigarette, a vented recess filter cigarette, a cigar, snuff, and chewing tobacco.

In an aspect, the present invention includes a tobacco product prepared from the tobacco plant, or part thereof, produced by growing a seed of tobacco cultivar ALBEX1F, a representative sample seed of the cultivar having been deposited with the ATCC under ATCC Accession No. PTA-11716, wherein said product is selected from the group consisting of pipe tobacco, cigar tobacco, cigarette tobacco, chewing tobacco, leaf tobacco, shredded tobacco, and cut tobacco, and wherein said product is further selected from the group consisting of a cigarillo, a non-ventilated recess filter cigarette, a vented recess filter cigarette, a cigar, snuff, and chewing tobacco, wherein said product has a reduced amount of nornicotine and/or N'-nitrosonornicotine (NNN) and/or more stably low nicotine conversion as compared to a product prepared from TN 90 or most other commercial burley tobacco cultivars grown and processed under similar conditions.

In an aspect, the present invention includes a part of the plant produced by growing a seed of tobacco cultivar ALBEX1F, a representative sample seed of the cultivar having been deposited with the ATCC under ATCC Accession No. PTA-11716, where the plant part is selected from the group consisting of leaf, pollen, ovule, embryo, cotyledon, hypocotyl, meristematic cell, protoplast, root, root tip, pistil, anther, flower, shoot, stem, pod and petiole.

In an aspect, the present invention includes a tissue culture produced from a protoplast or cell from the plant produced by growing a seed of tobacco cultivar ALBEX1F, a representative sample seed of the cultivar having been deposited with the ATCC under ATCC Accession No. PTA-11716, wherein said cell or protoplast of the tissue culture is produced from a plant part selected from the group consisting of a leaf, pollen, embryo, cotyledon, hypocotyl, meristematic cell, root, root tip, pistil, anther, flower, shoot, stem, pod and petiole.

In an aspect, the present invention includes a tobacco plant regenerated from a tissue culture produced from a protoplast or cell from the plant produced by growing a seed of tobacco cultivar ALBEX1F, a representative sample seed of the cultivar having been deposited with the ATCC under ATCC Accession No. PTA-11716, wherein said cell or protoplast of the tissue culture is produced from a plant part selected from the group consisting of a leaf, pollen, embryo, cotyledon, hypocotyl, meristematic cell, root, root tip, pistil, anther, flower, shoot, stem, pod and petiole, wherein the plant has essentially all of the morphological and physiological characteristics of cultivar ALBEX1F grown under similar conditions.

In another aspect, the present invention includes a seed of tobacco cultivar ALBEX1MS, a representative sample seed of the cultivar having been deposited with the ATCC under ATCC Accession No. PTA-11717 on behalf of Altria Client Services Inc. on Feb. 28, 2011.

In an aspect, the present invention provides a tobacco plant, or a part thereof, produced by growing a seed of tobacco cultivar ALBEX1MS, a representative sample seed of the cultivar having been deposited with the ATCC under ATCC Accession No. PTA-11717.

In an aspect, the present invention provides a harvested leaf of a tobacco plant, or part thereof, produced by growing a seed of tobacco cultivar ALBEX1MS, a representative sample seed of the cultivar having been deposited with the ATCC under ATCC Accession No. PTA-11717.

In an aspect, the present invention provides a harvested leaf of a tobacco plant, or part thereof, produced by growing a seed of tobacco cultivar ALBEX1MS, a representative sample seed of the cultivar having been deposited with the ATCC under ATCC Accession No. PTA-11717, wherein said leaf has a reduced amount of nornicotine and/or N'-nitrosonornicotine (NNN) and/or more stably low nicotine conversion as compared to a leaf from TN 90 or most other commercial burley tobacco cultivars grown under similar conditions.

In an aspect, the present invention provides a harvested leaf of a tobacco plant, or part thereof, produced by growing a seed of tobacco cultivar ALBEX1MS, a representative sample seed of the cultivar having been deposited with the ATCC under ATCC Accession No. PTA-11717, wherein said leaf has a reduced amount of nornicotine and/or N'-nitrosonornicotine (NNN), and wherein said reduced amount of nornicotine and/or N'-nitrosonornicotine (NNN) is reduced in a smoke stream produced from said leaf as compared to a leaf from TN 90 or most other commercial burley tobacco cultivars grown under similar conditions.

In an aspect, the present invention provides a tobacco product prepared from the tobacco plant, or part thereof, produced by growing a seed of tobacco cultivar ALBEX1MS, a representative sample seed of the cultivar having been deposited with the ATCC under ATCC Accession No. PTA-11717, wherein said product is selected from the group consisting of pipe tobacco, cigar tobacco, cigarette tobacco, chewing tobacco, leaf tobacco, shredded tobacco, and cut tobacco.

In an aspect, the present invention provides a tobacco product prepared from the tobacco plant, or part thereof, produced by growing a seed of tobacco cultivar ALBEX1MS, a representative sample seed of the cultivar having been deposited with the ATCC under ATCC Accession No. PTA-11717, wherein said product is selected from the group consisting of pipe tobacco, cigar tobacco, cigarette tobacco, chewing tobacco, leaf tobacco, shredded tobacco, and cut tobacco, wherein said product is selected from the group consisting of a cigarillo, a non-ventilated recess filter cigarette, a vented recess filter cigarette, a cigar, snuff, and chewing tobacco.

In an aspect, the present invention provides a product prepared from the tobacco plant, or part thereof, produced by growing a seed of tobacco cultivar ALBEX1MS, a representative sample seed of the cultivar having been deposited with the ATCC under ATCC Accession No. PTA-11717, wherein said product is selected from the group consisting of pipe tobacco, cigar tobacco, cigarette tobacco, chewing tobacco, leaf tobacco, shredded tobacco, and cut tobacco, wherein said product is selected from the group consisting of a cigarillo, a non-ventilated recess filter cigarette, a vented recess filter cigarette, a cigar, snuff, and chewing tobacco, wherein said product has a reduced amount of nornicotine and/or N'-nitrosonornicotine (NNN) and/or more stably low nicotine conversion as compared to a product prepared from TN 90 or most other commercial burley tobacco cultivars grown under similar conditions.

In an aspect, the present invention provides a part of a plant produced by growing a seed of tobacco cultivar ALBEX1MS, a representative sample seed of the cultivar having been deposited with the ATCC under ATCC Accession No. PTA-11717, where the part of the plant is selected from the group consisting of leaf, pollen, ovule, embryo, cotyledon, hypocotyl, meristematic cell, protoplast, root, root tip, pistil, anther, flower, shoot, stem, pod and petiole.

In an aspect, the present invention provides a tissue culture produced from a protoplast or cell from the plant produced by growing a seed of tobacco cultivar ALBEX1MS, a representative sample seed of the cultivar having been deposited with the ATCC under ATCC Accession No. PTA-11717, where said cell or protoplast of the tissue culture is produced from a plant part selected from the group consisting of a leaf, pollen, embryo, cotyledon, hypocotyl, meristematic cell, root, root tip, pistil, anther, flower, shoot, stem, pod and petiole.

In an aspect, the present invention provides a tobacco plant regenerated from a tissue culture produced from a protoplast or cell from the plant produced by growing a seed of tobacco cultivar ALBEX1MS, a representative sample seed of the cultivar having been deposited with the ATCC under ATCC Accession No. PTA-11717, where said cell or protoplast of the tissue culture is produced from a plant part selected from the group consisting of a leaf, pollen, embryo, cotyledon, hypocotyl, meristematic cell, root, root tip, pistil, anther, flower, shoot, stem, pod and petiole, wherein the plant has essentially all of the morphological and physiological characteristics of cultivar ALBEX1MS grown under similar conditions.

In an aspect, the present invention includes an $F_1$ progeny plant of tobacco cultivar ALBEX1F, a representative sample seed of the cultivar having been deposited with the ATCC under ATCC Accession No. PTA-11716.

The $F_1$ progeny plant of tobacco cultivar ALBEX1F, a representative sample seed of the cultivar having been deposited with the ATCC under ATCC Accession No. PTA-11716, wherein said $F_1$ plant is male sterile (MS).

In an aspect, the present invention includes an $F_1$ progeny plant of tobacco cultivar ALBEX1MS, a representative sample seed of the cultivar having been deposited with the ATCC under ATCC Accession No. PTA-11717.

In an aspect, the present invention provides a method for producing a tobacco seed comprising crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716.

In an aspect, the present invention provides a method for producing a tobacco seed comprising crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716, wherein the ALBEX1F plant is the female parent.

In an aspect, the present invention provides a method for producing a tobacco seed comprising crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716, wherein the other tobacco plant is male sterile (MS).

In an aspect, the present invention provides an $F_1$ progeny seed produced by a method of crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716, wherein the other tobacco plant is male sterile (MS).

In an aspect, the present invention provides a container of $F_1$ progeny seeds produced by a method of crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716, wherein the other tobacco plant is male sterile (MS).

In an aspect, the present invention provides an $F_1$ progeny plant produced by growing a seed produced by a method of crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716, wherein the other tobacco plant is male sterile (MS).

In an aspect, the present invention provides a harvested leaf of a tobacco plant, or part thereof, of an $F_1$ progeny plant produced by growing a seed produced by a method of crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716, wherein the other tobacco plant is male sterile (MS).

In an aspect, the present invention provides a harvested leaf of an $F_1$ progeny plant produced by growing a seed produced by a method of crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716, wherein the other tobacco plant is male sterile (MS), wherein said leaf has a reduced amount of nornicotine and/or N'-nitrosonornicotine (NNN) and/or more stably low nicotine conversion as compared to a leaf from TN 90 or most other commercial burley tobacco cultivars grown under similar conditions.

In an aspect, the present invention provides a harvested leaf of an $F_1$ progeny plant produced by growing a seed produced by a method of crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716, wherein the other tobacco plant is male sterile (MS), wherein said leaf has a reduced amount of nornicotine and/or N'-nitrosonornicotine (NNN) and/or more stably low nicotine conversion as compared to a leaf from TN 90 or most other commercial burley tobacco cultivars grown under similar conditions, wherein said reduced amount of nornicotine and/or N'-nitrosonornicotine (NNN) is reduced in a smoke stream produced from said leaf as compared to a leaf from TN 90 or most other commercial burley tobacco cultivars grown under similar conditions.

In an aspect, the present invention provides a tobacco product, prepared from an $F_1$ progeny plant produced by growing a seed produced by a method of crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716, wherein the other tobacco plant is male sterile (MS), wherein said product is selected from the group consisting of pipe tobacco, cigar tobacco, cigarette tobacco, chewing tobacco, leaf tobacco, shredded tobacco, and cut tobacco.

In an aspect, the present invention provides a tobacco product prepared from an $F_1$ progeny plant produced by growing a seed produced by a method of crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716, wherein the other tobacco plant is male sterile (MS), wherein said product is selected from the group consisting of pipe tobacco, cigar tobacco, cigarette tobacco, chewing tobacco, leaf tobacco, shredded tobacco, and cut tobacco, and wherein said product is further selected from the group consisting of a cigarillo, a non-ventilated recess filter cigarette, a vented recess filter cigarette, a cigar, snuff, and chewing tobacco.

In an aspect, the present invention provides a tobacco product prepared from an $F_1$ progeny plant produced by growing a seed produced by a method of crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716, wherein the other tobacco plant is male sterile (MS), wherein said product is selected from the group consisting of pipe tobacco, cigar tobacco, cigarette tobacco, chewing tobacco, leaf tobacco, shredded tobacco, and cut tobacco, and wherein said product is further selected from the group consisting of a cigarillo, a non-ventilated recess filter cigarette, a vented recess filter cigarette, a cigar, snuff, and chewing tobacco, wherein said product has a reduced amount of nornicotine and/or N'-nitrosonornicotine (NNN) and/or more stably low nicotine conversion as compared to a product prepared from TN 90 or most other commercial burley tobacco cultivars grown under similar conditions.

In an aspect, the present invention provides a method for producing a tobacco seed comprising crossing two tobacco plants and harvesting the resultant tobacco seed, wherein at least one tobacco plant is a tobacco plant of tobacco cultivar ALBEX1F, a representative sample seed of the cultivar having been deposited with the ATCC under ATCC Accession No. PTA-11716, wherein the other tobacco plant is male sterile (MS), wherein said MS plant is a plant of tobacco cultivar ALBEX1MS, a representative sample seed of said cultivar having been deposited with the ATCC under ATCC Accession No. PTA-11717.

In an aspect, the present invention includes a method of vegetatively propagating a plant of a tobacco cultivar comprising the steps of (a) collecting tissue capable of being propagated from a plant of a tobacco cultivar selected from the group consisting of ALBEX1F, a representative sample seed of the cultivar having been deposited with the ATCC under ATCC Accession No. PTA-11716, and ALBEX1MS; (b) cultivating the tissue to obtain a proliferated shoot; and (c) rooting the proliferated shoots to obtain a rooted plantlet.

In an aspect, the present invention includes a method of vegetatively propagating a plant of a tobacco cultivar comprising the steps of (a) culturing tissue capable of being propagated from a plant of a tobacco cultivar selected from the group consisting of ALBEX1F, a representative sample seed of the cultivar having been deposited with the ATCC under ATCC Accession No. PTA-11716, and ALBEX1MS to obtain a proliferated shoot; and (b) rooting the proliferated shoots to obtain a rooted plantlet, where the method further comprises growing a plant from said rooted plantlet In an aspect, the present invention includes a method of introducing a desired trait into a tobacco cultivar comprising: (a) crossing a plant of a tobacco cultivar selected from the group consisting of ALBEX1F, a representative sample seed of the cultivar having been deposited with the ATCC under ATCC Accession No. PTA-11716, and ALBEX1MS, a representative sample seed of the cultivar having been deposited with the ATCC under ATCC Accession No. PTA-11717, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of a tobacco cultivar selected from the group consisting of ALBEX1F and ALBEX1MS to produce a backcross $F_2$ progeny seed; (d) growing the $F_2$ progeny seed and selecting a backcross $F_2$ progeny plant comprising the desired trait; and (e) repeating steps (c) and (d) three or more times in succession to produce selected fourth or higher backcross progeny that comprise the desired trait and essentially all of the physiological and morphological characteristics of a tobacco cultivar selected from the group consisting of ALBEX1F and ALBEX1MS.

In an aspect, the present invention provides a method of introducing a desired trait into a tobacco cultivar comprising: (a) crossing a plant of a tobacco cultivar selected from the group consisting of ALBEX1F, a representative sample seed of the cultivar having been deposited with the ATCC under ATCC Accession No. PTA-11716, and ALBEX1MS, a representative sample seed of the cultivar having been deposited with the ATCC under ATCC Accession No. PTA-11717, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of a tobacco cultivar selected from the group consisting of ALBEX1F and ALBEX1MS to produce a backcross $F_2$ progeny seed; (d) growing the $F_2$ progeny seed and selecting a backcross $F_2$ progeny plant comprising the desired trait; and (e) repeating steps (c) and (d) three or more times in succession to produce selected fourth or higher backcross progeny that comprise the desired trait and essentially all of the physiological and morphological characteristics of a tobacco cultivar selected from the group consisting of ALBEX1F and ALBEX1MS, wherein said trait is male sterility (MS).

In an aspect, the present invention provides a method of introducing a desired trait into a tobacco cultivar comprising: (a) crossing a plant of a tobacco cultivar selected from the group consisting of ALBEX1F, a representative sample seed of the cultivar having been deposited with the ATCC under ATCC Accession No. PTA-11716, and ALBEX1MS, a representative sample seed of the cultivar having been deposited with the ATCC under ATCC Accession No. PTA-11717, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of a tobacco cultivar selected from the group consisting of ALBEX1F and ALBEX1MS to produce a backcross $F_2$ progeny seed; (d) growing the $F_2$ progeny seed and selecting a backcross $F_2$ progeny plant comprising the desired trait; and (e) repeating steps (c) and (d) three or more times in succession to produce selected fourth or higher backcross progeny that comprise the desired trait, and essentially all of the physiological and morphological characteristics of a tobacco cultivar selected from the group consisting of ALBEX1F and ALBEX1MS wherein said trait is male sterility (MS), and further where said MS trait is obtained from the cytoplasm of *Nicotiana suaveolens*.

In an aspect, the present invention provides a method of introducing a desired trait into a tobacco cultivar comprising:

(a) crossing a plant of a tobacco cultivar selected from the group consisting of ALBEX1F, a representative sample seed of the cultivar having been deposited with the ATCC under ATCC Accession No. PTA-11716, and ALBEX1MS, a representative sample seed of the cultivar having been deposited with the ATCC under ATCC Accession No. PTA-11717, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of a tobacco cultivar selected from the group consisting of ALBEX1F and ALBEX1MS to produce a backcross $F_2$ progeny seed; (d) growing the $F_2$ progeny seed and selecting a backcross $F_2$ progeny plant comprising the desired trait; and (e) repeating steps (c) and (d) three or more times in succession to produce selected fourth or higher backcross progeny that comprise the desired trait and essentially all of the physiological and morphological characteristics of a tobacco cultivar selected from the group consisting of ALBEX1F and ALBEX1MS, wherein said trait is male sterility (MS), where said MS trait is obtained from the cytoplasm of *Nicotiana suaveolens*, and further wherein said second tobacco plant is MS TN 90.

In an aspect, the present invention provides a tobacco plant produced by a method of introducing a desired trait into a tobacco cultivar comprising: (a) crossing a plant of a tobacco cultivar selected from the group consisting of ALBEX1F, a representative sample seed of the cultivar having been deposited with the ATCC under ATCC Accession No. PTA-11716, and ALBEX1MS, a representative sample seed of the cultivar having been deposited with the ATCC under ATCC Accession No. PTA-11717, with a second tobacco plant that comprises a desired trait to produce an $F_1$ progeny seed; (b) growing the $F_1$ progeny seed and selecting an $F_1$ progeny plant that comprises the desired trait; (c) crossing the selected $F_1$ progeny plant with a plant of a tobacco cultivar selected from the group consisting of ALBEX1F and ALBEX1MS to produce a backcross $F_2$ progeny seed; (d) growing the $F_2$ progeny seed and selecting a backcross $F_2$ progeny plant comprising the desired trait; and (e) repeating steps (c) and (d) three or more times in succession to produce selected fourth or higher backcross progeny that comprise the desired trait and essentially all of the physiological and morphological characteristics of a tobacco cultivar selected from the group consisting of ALBEX1F and ALBEX1MS, wherein said trait is male sterility (MS).

In another aspect, the present invention includes a method of introducing a desired trait into a tobacco cultivar comprising: (a) crossing a plant of a tobacco cultivar selected from the group consisting of ALBEX1F, a representative sample seed of the cultivar having been deposited with the ATCC under ATCC Accession No. PTA-11716, and ALBEX1MS, a representative sample seed of the cultivar having been deposited with the ATCC under ATCC Accession No. PTA-11717, with a plant of another tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing; small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of a tobacco cultivar selected from the group consisting of ALBEX1F and ALBEX1MS to produce a backcross progeny plant seed; (d) growing the backcross progeny plant seed into a backcross progeny plant and selecting the backcross progeny plant comprising the desired trait; and (e) repeating steps (c) and (d) one or more times in succession to produce a selected fourth or higher backcross progeny plant that comprises the desired trait and essentially all of the physiological and morphological characteristics of a tobacco cultivar selected from the group consisting of ALBEX1F and ALBEX1MS grown under similar conditions.

In an aspect, the present invention includes a tobacco plant produced by a method of introducing a desired trait into a tobacco cultivar comprising: (a) crossing a plant of a tobacco cultivar selected from the group consisting of ALBEX1F, a representative sample seed of the cultivar having been deposited with the ATCC under ATCC Accession No. PTA-11716, and ALBEX1MS, a representative sample seed of the cultivar having been deposited with the ATCC under ATCC Accession No. PTA-11717, with a plant of another tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing; small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of a tobacco cultivar selected from the group consisting of ALBEX1F and ALBEX1MS to produce a backcross progeny plant seed; (d) growing the backcross progeny plant seed into a backcross progeny plant and selecting the backcross progeny plant comprising the desired trait; and (e) repeating steps (c) and (d) one or more times in succession to produce a selected fourth or higher backcross progeny plant that comprises the desired trait and essentially all of the physiological and morphological characteristics of a tobacco cultivar selected from the group consisting of ALBEX1F and ALBEX1MS grown under similar conditions, wherein the plant has said desired trait.

In an aspect, the present invention includes a tobacco plant produced by a method of introducing a desired trait into a tobacco cultivar comprising: (a) crossing a plant of a tobacco cultivar selected from the group consisting of ALBEX1F, a representative sample seed of the cultivar having been deposited with the ATCC under ATCC Accession No. PTA-11716, and ALBEX1MS, a representative sample seed of the cultivar having been deposited with the ATCC under ATCC Accession No. PTA-11717, with a plant of another tobacco cultivar that comprises a desired trait to produce a progeny plant where the desired trait is selected from the group consisting of herbicide resistance, pest resistance, disease resistance, high yield, high grade index, curability, curing quality, mechanical harvestability, holding ability, leaf quality, height, plant maturation, early maturing, early to medium maturing, medium maturing, medium to late maturing, late maturing; small stalk, medium stalk, large stalk, leaf number per plant, 5-10 leaves per plant, 11-15 leaves per plant, 16-21 leaves per plant, and any combination thereof, to produce an $F_1$ progeny seed; (b) growing the $F_1$ progeny seed into an $F_1$ progeny plant and selecting the $F_1$ progeny plant having the desired trait; (c) crossing the selected $F_1$ progeny plant with a plant of a tobacco cultivar selected from the group consisting of ALBEX1F and ALBEX1MS to produce a backcross progeny plant seed; (d) growing the backcross progeny plant seed into a backcross progeny plant and selecting the backcross progeny plant comprising the desired trait; and (e) repeating steps (c) and (d) one or more times in succession to produce a selected fourth or higher backcross progeny plant that comprises the desired trait and essentially all of the physiological and morphological characteristics of a tobacco cultivar selected from the group consisting of ALBEX1F and ALBEX1MS grown under similar conditions, wherein the plant has the desired trait, and wherein the desired trait is herbicide resistance.

In another aspect, the present invention includes a method for producing a tobacco plant having decreased nicotine conversion comprising: identifying a first tobacco plant having the sequence set forth in SEQ ID NO: 1; crossing the first tobacco plant with a second tobacco plant and collecting an $F_1$ seed; crossing a plant grown from the $F_1$ seed to a third tobacco plant; and identifying a tobacco plant that is homozygous for the sequence set forth in SEQ ID NO: 1.

In an aspect, the present invention includes a method for producing a tobacco plant having decreased nicotine conversion comprising: identifying a first tobacco plant having the sequence set forth in SEQ ID NO: 1; crossing the first tobacco plant with a second tobacco plant and collecting an $F_1$ seed; crossing a plant grown from the $F_1$ seed to a third tobacco plant; and identifying a tobacco plant that is homozygous for the sequence set forth in SEQ ID NO: 1, wherein said second tobacco plant has the sequence set forth in SEQ ID NO: 1.

In an aspect, the present invention includes a method for producing a tobacco plant having decreased nicotine conversion comprising: identifying a first tobacco plant having the sequence set forth in SEQ ID NO: 1; crossing the first tobacco plant with a second tobacco plant and collecting an $F_1$ seed; crossing a plant grown from the $F_1$ seed to a third tobacco plant; and identifying a tobacco plant that is homozygous for the sequence set forth in SEQ ID NO: 1, wherein said second tobacco plant does not have the sequence set forth in SEQ ID NO: 1 and said third tobacco plant is a tobacco plant having the sequence set forth in SEQ ID NO: 1.

In an aspect, the present invention includes a method for producing a tobacco plant having decreased nicotine conversion comprising: identifying a first tobacco plant having the sequence set forth in SEQ ID NO: 1; crossing the first tobacco plant with a second tobacco plant and collecting an $F_1$ seed; crossing a plant grown from the $F_1$ seed to a third tobacco plant; and identifying a tobacco plant that is homozygous for the sequence set forth in SEQ ID NO: 1, wherein said first tobacco plant is a plant of a tobacco cultivar selected from the group consisting of ALBEX1F, a representative sample seed of said cultivar having been deposited with the ATCC under ATCC Accession No. PTA-11716, and ALBEX1MS, a representative sample seed of said cultivar having been deposited with the ATCC under ATCC Accession No. PTA-11717.

In an aspect, the present invention includes a method for producing a tobacco plant having decreased nicotine conversion comprising: identifying a first tobacco plant having the sequence set forth in SEQ ID NO: 1; crossing the first tobacco plant with a second tobacco plant and collecting an $F_1$ seed; crossing a plant grown from the $F_1$ seed to a third tobacco plant; and identifying a tobacco plant that is homozygous for the sequence set forth in SEQ ID NO: 1, wherein said first tobacco plant is a plant of a tobacco cultivar selected from the group consisting of ALBEX1F, a representative sample seed of said cultivar having been deposited with the ATCC under ATCC Accession No. PTA-11716, and ALBEX1MS, a representative sample seed of said cultivar having been deposited with the ATCC under ATCC Accession No. PTA-11717, wherein said third tobacco plant is a plant of a tobacco cultivar selected from the group consisting of ALBEX1F, a representative sample seed of said cultivar having been deposited with the ATCC under ATCC Accession No. PTA-11716, ALBEX1MS, and a representative sample seed of said cultivar having been deposited with the ATCC under ATCC Accession No. PTA-11717.

In another aspect, the present invention includes a method of producing a plant of a tobacco cultivar selected from the group consisting of ALBEX1F and ALBEX1MS having an additional desired trait comprising the steps of: (a) collecting tissue capable of being propagated from a plant of a tobacco cultivar selected from the group consisting of ALBEX1F, a representative sample seed of the cultivar having been deposited with the ATCC under ATCC Accession No. PTA-11716 and ALBEX1MS, a representative sample seed of the cultivar having been deposited with the ATCC under ATCC Accession No. PTA-11717; and (b) introducing a transgene conferring the desired trait into the tissue.

In an aspect, the present invention includes a method of producing an herbicide resistant tobacco plant comprising transforming the tobacco plant produced by growing a seed of tobacco cultivar ALBEX1F, a representative sample seed of said cultivar having been deposited with the ATCC under ATCC Accession No. PTA-11716 with a transgene wherein the transgene confers resistance to an herbicide selected from the group consisting of imidazolinone, cyclohexanedione, sulfonylurea, glyphosate, glufosinate, phenoxy proprionic acid, L-phosphinothricin, triazine and benzonitrile.

In an aspect, the present invention includes an herbicide resistant tobacco plant produced by a method of producing an herbicide resistant tobacco plant comprising transforming the tobacco plant produced by growing a seed of tobacco cultivar ALBEX1F, a representative sample seed of said cultivar having been deposited with the ATCC under ATCC Accession No. PTA-11716 with a transgene wherein the transgene confers resistance to an herbicide selected from the group consisting of imidazolinone, cyclohexanedione, sulfonylurea, glyphosate, glufosinate, phenoxy proprionic acid, L-phosphinothricin, triazine and benzonitrile.

In an aspect, the present invention includes a method of producing a pest or insect resistant tobacco plant wherein the method comprises transforming the tobacco plant produced by a seed of tobacco cultivar ALBEX1F, a representative sample seed of said cultivar having been deposited with the ATCC under ATCC Accession No. PTA-11716 with a transgene that confers pest or insect resistance.

In an aspect, the present invention includes a pest or insect resistant tobacco plant produced by transforming the tobacco plant produced by a seed of tobacco cultivar ALBEX1F, a representative sample seed of said cultivar having been deposited with the ATCC under ATCC Accession No. PTA-11716 with a transgene that confers pest or insect resistance.

In an aspect, the present invention includes a pest or insect resistant tobacco plant produced by transforming the tobacco plant produced by a seed of tobacco cultivar ALBEX1F, a representative sample seed of said cultivar having been deposited with the ATCC under ATCC Accession No. PTA-11716 with a transgene that confers pest or insect resistance, wherein the transgene encodes a *Bacillus thuringiensis* (BT) endotoxin.

In an aspect, the present invention includes a method of producing a disease resistant tobacco plant wherein the method comprises transforming a tobacco plant produced by growing a seed of tobacco cultivar ALBEX1F, a representative sample seed of said cultivar having been deposited with the ATCC under ATCC Accession No. PTA-11716 with a transgene that confers disease resistance.

In an aspect, the present invention includes a disease resistant tobacco plant produced by transforming a tobacco plant produced by growing a seed of tobacco cultivar ALBEX1F, a representative sample seed of said cultivar having been deposited with the ATCC under ATCC Accession No. PTA-11716 with a transgene that confers disease resistance.

BRIEF DESCRIPTION OF SEQUENCES

SEQ ID NO: 1 sets forth a cyp82e4 W329Stop nucleotide sequence.

SEQ ID NO: 2 sets forth a cyp82e4 W329Stop amino acid sequence.

SEQ ID NO: 3 sets forth a CYP82E4 wild-type nucleotide sequence.

SEQ ID NO: 4 sets forth a CYP82E4 wild-type amino acid sequence.

DETAILED DESCRIPTION OF THE INVENTION

ALBEX1F

The present invention includes tobacco cultivars, and parts thereof, from ALBEX1F, where representative sample seeds of this cultivar have been deposited with the ATCC under ATCC Accession No. PTA-11716. In another aspect, the present invention includes a tobacco plant, or a part thereof, produced by growing the seed of ALBEX1F. A plant of the present invention can include a plant with essentially all of the morphological and physiological characteristics of cultivar ALBEX1F grown under similar conditions.

While not being limited by process, ALBEX1F is a result of the introduction of a mutated CYP84 gene in a Tennessee 90 (non LC) ("TN 90") cultivar. The gene is a mutated CYP82E4 gene recited as 4246 in U.S. patent application Ser. No. 11/611,782, filed on Dec. 15, 2006 and published as US 2007/0199097 on Aug. 23, 2007 (SEQ ID NO: 1, which sets forth a cyp82e4 W329Stop, hereby incorporated by reference in its entirety). The mutation results in a truncated protein.

ALBEX1F is generated by backcrossing with TN 90 five times as the recurrent parent and selfing twice. ALBEX1F is homozygous for cyp82e4 W329Stop. Again, not limited by any particular scientific theory, a cyp82e4 W329Stop is recessive. A cyp82e4 W329Stop encodes for proteins with reduced or eliminated ability to convert nicotine to nornicotine. ALBEX1F has a genetic background that is at least 95%, at least 97%, at least 98%, or at least 99% similar to TN 90. ALBEX1FC exhibits low NNN and is not subject to conversion to high NNN's.

ALBEX1MS

The present invention also provides tobacco cultivars, and parts thereof, from ALBEX1MS, where representative sample seeds of this cultivar have been deposited with the ATCC under ATCC Accession No. PTA-11717. The present invention also includes a tobacco plant, or a part thereof, produced by growing a seed of ALBEX1MS. A plant of the present invention can include a plant with essentially all of the morphological and physiological characteristics of cultivar ALBEX1MS grown under similar conditions. While not being limited by process, ALBEX1MS is a result of introducing the cyp82e4 W329Stop mutation from a $BC_5F_1$ TN 90 and crossed as the male parent to TN 90 male sterile ("MS") to prepare MS $F_1$ progeny plants.

The MS $F_1$ progeny plants of the $BC_5F_1 \times MS$ TN 90 cross are male sterile. These MS $F_1$ progeny plants (e.g., $BC_6F_1$ MS) are screened for the cyp82e4 W329Stop mutation. Similarly, the $BC_5F_1$ is crossed with a TN 90 to yield a fertile $BC_6F_1$ plant that is screened for the mutation. The MS $F_1$ progeny plant, identified as having the mutation, is the female parent in a subsequent cross with the fertile male parent $BC_6F_1$, which also has the mutation. Progeny of this cross (e.g., $BC_7F_1$ MS progeny) are male sterile and those that are homozygous for the cyp82e4 W329Stop mutation are identified by genotyping and designated as ALBEX1MS. To maintain the line, plants of line ALBEX1MS plants are pollinated with a ALBEX1F plant. ALBEX1MS has a genetic background that is at least 95%, at least 97%, at least 98%, at least 99% similar to TN 90. ALBEX1MS exhibits low NNN and is not subject to conversion to high NNN's.

Other Plants

A progeny plant of the present application can be a plant of $F_1$, $F_2$, $F_3$, $F_4$ or later generation obtained by either crossing two parental plants or selfing one plant.

Under similar conditions as defined in the present application can be under similar environmental conditions or under similar laboratory conditions.

The present invention includes a tobacco seed produced by crossing two parent tobacco plants and harvesting the resultant tobacco seed, where at least one parent tobacco plant is ALBEX1F. In one aspect, the ALBEX1F is the female parent plant. In another aspect, the ALBEX1MS is the male parent plant. One aspect of the present invention provides tobacco plants that are homozygous at the cyp82e4 locus for SEQ ID NO: 1 which shares a genetic background that is greater than 75%, 80%, 85%, 90%, 95%, 98%, or 99% TN90. In one aspect, approximate or greater than 50%, 75%, or 100% of a progeny's genetics is provided by a plant of the present invention that is homozygous at the cyp82e4 locus for SEQ ID NO: 1. In one aspect, a plant of the present invention has a genetic background that is at least 95%, at least 97%, at least 98%, or at least 99% similar to TN 90. In another aspect, a plant of the present invention exhibits low NNN and is not subject to conversion to high NNN's. In one aspect, a plant of the present invention is the progeny plant of a female or male parent plant that is *Fusarium* wilt resistant.

In one aspect, a plant of the present invention is a medium-late maturing variety with moderately high yield potential. In another aspect, a plant of the present invention offers a broad range of important agronomic characteristics. In a further aspect, a plant of the present invention has one, two, three, four or more of the traits including moderate resistance to black shank, some tolerance to blue mold, black root rot resistance, and resistance to common virus diseases. In another aspect, a plant of the present invention has blue mold tolerance and level 4 resistance to both races of black shank and high root rot resistance. In one aspect, a plant of the present invention, such as ALBEX1F or ALBEX1MS, lacks *Fusarium* wilt resistance. In another aspect, a plant of the present invention is *Fusarium* wilt resistant.

In an aspect, the plants of the present invention have reduced or eliminated ability to convert nicotine to nornicotine as compared to TN 90 or most other commercial burley tobacco cultivars grown under similar conditions. In an aspect, the percentage nicotine conversion is less than 75%, 70%, 60%, 50%, or 25% of that found in TN90. The nicotine conversion in plants of the present invention, including ALBEX1F and ALBEX1MS, can be less than about 4%, 3-1%, 3-0.5%, 2-0.5%, about 2%, about 1%. In a preferred aspect, the percentage nicotine conversion is less than 25%, 10%, 5%, or 2% of that found in TN90 without a cyp82e4

W329Stop mutation. In an aspect, the tobacco plants of the present invention have a nicotine conversion rate of 3.5, 3.25, 3.0 or 2.75% or less. In another aspect, the nicotine conversion rate of tobacco plants of the present invention have can be 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6% or less. In another aspect, the nicotine conversion rates can be from 0.5 to 0.9%, 0.5 to 1.5%, 0.5 to 2.0%, 0.5 to 2.5%, 0.5 to 2.75%, and 0.5 to 3.0%. In another aspect, the nicotine conversion rates can be from 1.0 to 1.5%, 1.0 to 1.75%, 1.0 to 2.0%, 1.0 to 2.5%, 1.0 to 2.75%, and 1.0 to 3.0%. In another aspect, the nicotine conversion rate in a plant of the present invention may be less than 2.9, 2.75, 2.5, 2.25, 2.0, 1.9, 1.8, 1.7, 1.6, 1.5, 1.4, 1.3, 1.2, 1.1 or 1.0%. In an aspect, the tobacco plants of the present invention have a nicotine conversion rate of 3.5, 3.25, 3.0 or 2.75% or less. In another aspect, the nicotine conversion rate of tobacco plants of the present invention can be 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6% or less. In another aspect, the nicotine conversion rates can be from 0.5 to 0.9%, 0.5 to 1.5%, 0.5 to 2.0%, 0.5 to 2.5%, 0.5 to 2.75%, and 0.5 to 3.0%. In another aspect, the nicotine conversion rates can be from 1.0 to 1.5%, 1.0 to 1.75%, 1.0 to 2.0%, 1.0 to 2.5%, 1.0 to 2.75%, and 1.0 to 3.0%. In another aspect, the nicotine conversion rate in a plant of the present invention may be less than 2.9, 2.75, 2.5, 2.25, 2.0, 1.9, 1.8, 1.7, 1.6, 1.5, 1.4, 1.3, 1.2, 1.1 or 1.0%.

In another aspect, the tobacco plants of the present invention typically have a reduced amount of nornicotine of less than about 0.10% dry weight as compared to TN 90 or most other commercial burley tobacco cultivars grown and processed under similar conditions. For example, the nornicotine content in such plants can be 1.2, 1.0, 0.7, 0.5, 0.4, 0.2, 0.1, 0.075, 0.05, 0.025, 0.01, 0.009, 0.0075, 0.005, 0.0025, 0.001, 0.0009, 0.00075, 0.0005, 0.00025, 0.0001% dry weight, or undetectable. In another aspect, the nornicotine content can be less than 1.2, 1.0, 0.7, 0.5, 0.4, 0.2, 0.1, 0.075, 0.05, 0.025, 0.01, 0.009, 0.0075, 0.005, 0.0025, 0.001, 0.0009, 0.00075, 0.0005, 0.00025, 0.0001% dry weight. In another aspect, the nornicotine content in such plants can be from 1.2-1.0, 0.7-0.5, 0.4-0.2, 0.1-0.075, 0.05-0.025, 0.01-0.0075, 0.005-0.0025, 0.001-0.00075, 0.0005-0.00025, or 0.0005-0.0001% dry weight. In a plant of the present invention, the nornicotine is a relatively small percentage of total alkaloids in the plant compared to a commercial seedlot of TN90. The nornicotine in a plant of the present invention may be 2-1%, less than 3%, about 2%, about 1.5%, about 1%, or 0.75% percentage of total alkaloids. Tobacco products having a reduced amount of nitrosamine content and/or more stably low nicotine conversion as compared to a product prepared from TN 90 or most other commercial burley tobacco cultivars grown and processed under similar conditions can be manufactured using tobacco plant material from plants and plant parts of the present invention. The tobacco product typically has a reduced amount of nornicotine of less than about 3 mg/g. For example, the nornicotine content in such a product can be 3.0 mg/g, 2.5 mg/g, 2.0 mg/g, 1.5 mg/g, 1.0 mg/g, 750 μg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable. The tobacco product typically has a reduced amount of NNN of less than about 10 pg/g. For example, the NNN content in such a product can be about 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable. The percentage of secondary alkaloids relative to total alkaloid content contained in a plant of the present invention may not be statistically different than from a commercial seedlot of TN90.

Differences between two inbred tobacco varieties or two hybrid tobacco varieties can be evaluated using statistical approaches. Statistical analysis includes the calculation of mean values, determination of the statistical significance of the sources of variation, and the calculation of the appropriate variance components. Methods for determining statistical significance are known in the art. Statistical software is available, for example, the PROC GLM function of SAS. Significance is generally presented as a "p-value". A statistically significant p-value is less than 0.10. In a preferred aspect, the p-value is less than, or equal to, 0.05. In another aspect, the p-value is 0.04 or less, 0.03 or less, 0.02 or less. In yet another aspect, a statistically significant value is less than 0.01. In yet another aspect, it can be less than 0.009, less than 0.008, less than 0.007, less than 0.006, less than 0.005, less than 0.004, less than 0.003, less than 0.002, or less than 0.001.

Tobacco plants of the present invention that are homozygous for a cyp82e4 W329Stop allele have a reversion rate that is statistically significantly lower than corresponding control TN 90 plants having the wild-type nicotine demethylase CYP82E4 gene. In addition, homozygous CYP82E4 mutant tobacco plants have a percent conversion to nornicotine of less than 3%, e.g., 1 to 3%, 2 to 3%, 1.8 to 3.15%, 1.8 to 2.0%, or 1.0 to 2.0%. Plants of the present invention can also be non-converters with reduced reversion rates as set forth in U.S. patent application Ser. No. 11/611,782, filed on Dec. 15, 2006 and published as US 2007/0199097 on Aug. 23, 2007, hereby incorporated by reference in its entirety.

Nicotine and nornicotine can be measured in ethylene-treated leaves using methods known in the art (e.g., gas chromatography). Percent nicotine demethylation in a sample is calculated by dividing the level of nornicotine by the combined level of nicotine and nornicotine as measured in the sample, and multiplying by 100. Percent nicotine demethylation in a sample from a plant of the present invention is 50, 40, 30, 20, 10 percent of a sample from an individual plant grown from a commercial seedlot of TN 90.

In an aspect, the tobacco plants of the present invention have a USDA quality index of about 65. In another aspect, the quality index may be at least about 55, 60, 62.5 or greater. In another aspect, tobacco plants of the present invention can have a quality index of 60-65, 60-65, 60-65; 60-70, 62.5-65, 62.5-70, or 65-70.

A plant of the present invention, including ALBEX1F and ALBEX1MS, can have any yield, including high (e.g., over 3000 lbs/A), moderately high (e.g., 2200-3000 lbs/A), and moderate (e.g., less than 2000 lbs/A) yield potential.

In another aspect, the present invention also provides for a plant grown from the seed of a ALBEX1F or ALBEX1MS plant in which alkaloids obtained from tobacco plants grown for the seed have decreased nornicotine, as well as plant parts and tissue cultures from such plants, representative sample seeds of these cultivars having been deposited with the ATCC, respectively under ATCC Accession Nos. PTA-11716 and PTA-11717.

An aspect of the present invention provides for parts of the cultivars ALBEX1F and ALBEX1MS. For example, leaves, pollen, embryos, cotyledons, hypocotyls, roots, root tips, anthers, flowers, ovules, shoots, stems, stalks, pith and capsules, tissue culture comprising tissue, callus, cells or protoplasts of the cultivars ALBEX1F and ALBEX1MS. In another aspect, the present invention provides for parts from hybrids having cultivars ALBEX1F and ALBEX1MS as parents or ancestors, and ALBEX1F and ALBEX1MS derived tobacco plants. In yet another aspect, the present invention provides for parts from genetically modified (e.g., by conventional breeding or genetic engineering techniques) forms of the foregoing plants and tissue culture.

Additional aspects of the present invention provide products comprising tobacco wherein the tobacco further comprises tobacco from the plants of the present invention, and parts thereof. Other aspects of the invention provide cured plant leaves and other plant parts. Accordingly, in some aspects the cured plant parts include, but are not limited to, a leaf, pollen, ovule, embryo, cotyledon, hypocotyl, meristematic cell, protoplast, root, root tip, pistil, anther, flower, shoot, stem, pod, petiole, and the like, and combinations thereof.

Thus, in some aspects, the present invention provides a cured tobacco comprising the leaves of the tobacco plant designated ALBEX1F, a representative sample seed of said cultivar having been deposited with the ATCC under ATCC Accession No. PTA-11716. In another aspect the present invention provides a cured tobacco comprising the leaves of the tobacco plant designated ALBEX1MS, a representative sample seed of said cultivar having been deposited with the ATCC under ATCC Accession No. PTA-11717.

Thus, in some aspects, the present invention provides a cured tobacco comprising the stems of the tobacco plant designated ALBEX1F, a representative sample seed of said cultivar having been deposited with the ATCC under ATCC Accession No. PTA-11716. In another aspect the present invention provides a cured tobacco comprising the stems of the tobacco plant designated ALBEX1MS, a representative sample seed of said cultivar having been deposited with the ATCC under ATCC Accession No. PTA-11717.

In still other aspects, the present invention provides a cured tobacco comprising the leaves and stems of the tobacco plants designated ALBEX1F and ALBEX1MS, representative sample seeds of these cultivars having been deposited with the ATCC, respectively under ATCC Accession Nos. PTA-11716 and PTA-11717.

The present invention also provides a container of ALBEX1F or ALBEX1MS seeds or other seeds of the present invention in which alkaloids obtained from tobacco plants grown from greater than 50% of the seeds have decreased nornicotine. In another aspect, alkaloids obtained from ALBEX1F or ALBEX1MS plants or other plants of the present invention grown from greater than 55%, 60%, 65%, 70%, 75%, 80%, 85%, 90%, 95% of the seeds in the container have decreased nornicotine, representative sample seeds of these cultivars having been deposited with the ATCC, respectively under ATCC Accession Nos. PTA-11716 and PTA-11717.

The container of ALBEX1F or ALBEX1MS seeds or other seeds of the present invention may contain any number, weight or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Representative sample seeds of ALBEX1F and ALBEX1MS cultivars having been deposited with the ATCC, respectively under ATCC Accession Nos. PTA-11716 and PTA-11717.

Containers of ALBEX1F or ALBEX1MS seeds or other seeds of the present invention may be any container available in the art. By way of a non-limiting example, a container may be a box, a bag, a packet, a pouch, a tape roll, a pail, a foil, or a tube, representative sample seeds of these cultivars having been deposited with the ATCC. Representative sample seeds of ALBEX1F and ALBEX1MS cultivars have been deposited with the ATCC, respectively under ATCC Accession Nos. PTA-11716 and PTA-11717.

In another aspect, the present invention also provides a container of ALBEX1F or ALBEX1MS in which greater than 50% of ALBEX1F or ALBEX1MS seeds or other seeds of the present invention have decreased nornicotine, representative sample seeds of these cultivars having been deposited with the ATCC. Representative sample seeds of ALBEX1F and ALBEX1MS cultivars have been deposited with the ATCC, respectively under ATCC Accession Nos. PTA-11716 and PTA-11717.

In one aspect, the present invention provides a seed of a ALBEX1F or ALBEX1MS plant or other plant of the present invention in which a plant grown from a seed is male sterile. Representative sample seeds of ALBEX1F and ALBEX1MS cultivars have been deposited with the ATCC, respectively under ATCC Accession Nos. PTA-11716 and PTA-11717.

Tobacco material obtained from the tobacco lines, varieties or hybrids of the present invention can be used to make tobacco products including, without limitation, cigarette products (e.g., cigarettes and bidi cigarettes), cigar products (e.g., cigar wrapping tobacco and cigarillos), pipe tobacco products, smokeless cigarette products, smokeless tobacco products (e.g., moist snuff, dry snuff, and chewing tobacco), films, chewables, tabs, shaped parts, gels, consumable units, insoluble matrices, hollow shapes and the like. See, e.g., U.S. Patent Publication No. US 2006/0191548, which is herein incorporated by reference in its entirety.

Tobacco products derived from plants of the present invention also include cigarettes and other smoking articles, particularly those smoking articles including filter elements, wherein the rod of smokeable material includes cured tobacco within a tobacco blend. In an aspect, a tobacco product may be pipe tobacco, cigar tobacco, cigarette tobacco, chewing tobacco, leaf tobacco, shredded tobacco, and cut tobacco.

In an aspect, the tobacco product of the present invention can be a blended tobacco product. In other aspects of the invention, the tobacco product of the present invention can be a reduced nicotine tobacco product as compared to a product prepared from TN 90 or most other commercial burley tobacco cultivars grown and processed under similar conditions. In still other aspects, the tobacco product of the present invention can be a blended tobacco product with reduced nicotine content as compared to a product prepared from TN 90 or most other commercial burley tobacco cultivars grown and processed under similar conditions. Thus, the tobacco product of the present invention can be a blended reduced nicotine tobacco product as compared to a product prepared from TN 90 or most other commercial burley tobacco cultivars grown and processed under similar conditions. Tobacco product material comprises a blend of tobacco materials from the present invention, wherein the blend comprises at least about 5, 10, 20, 30, 40, 50, 60, 70, 80, 90, or 95 percent by weight of a cured tobacco, based on the dry weight of the tobacco material. US 2008/0245377 is herein incorporated by reference for blend mixtures in its entirety.

In an aspect, tobacco products having a reduced amount of nitrosamine content and/or more stably low nicotine conversion as compared to a product prepared from TN 90 or most other commercial burley tobacco cultivars grown and processed under similar conditions can be manufactured using tobacco plant material from plants and plant parts of the present invention. The tobacco product typically has a reduced amount of nornicotine of less than about 3 mg/g. For example, the nornicotine content in such a product can be 3.0 mg/g, 2.5 mg/g, 2.0 mg/g, 1.5 mg/g, 1.0 mg/g, 750 µg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable. The tobacco product typically has a reduced amount of NNN of less than about 10 pg/g. For example, the nornicotine content in such a product can be about 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable. The percentage of secondary alkaloids relative to total alkaloid content contained in a plant of the present invention may not be statistically different than from a commercial seedlot of TN90 LC.

A tobacco plant of the present invention designated ALBEX1F or ALBEX1MS, carrying a cyp82e4 W329Stop allele can be used in a plant breeding program to create useful lines, cultivars, varieties, progeny, inbreds, and hybrids. Thus, in some aspects, an $F_1$, $F_2$, $F_3$, or later generation tobacco plant containing a cyp82e4 W329Stop alleles is crossed with a second *Nicotiana* plant, and progeny of the cross are identified in which a cyp82e4 W329Stop allele is present. It will be appreciated that the second *Nicotiana* plant will be ALBEX1F or ALBEX1MS, optionally with an additional desirable trait, such as herbicide resistance mentioned below. It will also be appreciated that the second TN90 or TN90 LC *Nicotiana* plant will contain a cyp82e4 W329Stop allele.

In still other aspects, methods of the present invention further include self-pollinating or pollinating a male sterile pollen acceptor with a pollen donor capable of being used in production of a progeny of the present invention, such as a male sterile hybrid of the present invention. Either the male sterile pollen acceptor plant or the pollen donor plant has at least one mutant allele, at a nicotine demethylase locus, such as cyp82e4 W329Stop. In an aspect, an allele at a nicotine demethylase locus is a mutant allele, making the plant homozygous for cyp82e4 W329Stop.

Breeding can be carried out via any known procedures. DNA fingerprinting, SNP or similar technologies may be used in a marker-assisted selection (MAS) breeding program to transfer or breed mutant alleles of a nicotine demethylase gene into other tobaccos. For example, a breeder can create segregating populations from hybridizations of a genotype containing a cyp82e4 W329Stop allele with an agronomically desirable genotype. Plants in the $F_2$ or backcross generations can be screened using a marker developed from a cyp82e4 W329Stop allele or a fragment thereof, using one of the techniques known in the art or listed herein. Plants identified as possessing a cyp82e4 W329Stop allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered. A recurrent parent in the present invention can be ALBEX1F or TN 90. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

*Nicotiana* species which exhibit breeding compatibility with *Nicotiana tabacum* include *Nicotiana amplexicaulis*, PI 271989; *Nicotiana benthamiana* PI 555478; *Nicotiana bigelovii* PI 555485; *Nicotiana debneyi*; *Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica*; *Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572. See also, Compendium of Tobacco Diseases published by American Phytopathology Society, or The Genus *Nicotiana* Illustrated, published by Japan Tobacco Inc, hereby incorporated by reference in their entirety.

The result of a plant breeding program using the mutant tobacco plants described herein includes useful lines, cultivars, varieties, progeny, inbreds, and hybrids. As used herein, the term 'variety' refers to a population of plants that share constant characteristics which separate them from other plants of the same species. A variety is often, although not always, sold commercially. While possessing one or more distinctive traits, a variety is further characterized by a very small overall variation between individuals within that variety. A 'pure line' variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972, on Oct. 23, 1978, and on Mar. 19, 1991), a variety is 'essentially derived' from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A 'line' as distinguished from a variety most often denotes a group of plants used non-commercially, for example in plant research. A line typically displays little overall variation between individuals for one or more traits of interest, although there may be some variation between individuals for other traits.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility wherein a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting $F_1$ seed is harvested.

Plants can be used to form single-cross tobacco $F_1$ hybrids. In such an aspect, the plants of the parent varieties can be grown as substantially homogeneous adjoining populations to facilitate natural cross-pollination from the male parent plants to the female parent plants. The $F_1$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

Successful crosses yield $F_1$ plants that are fertile, have a cyp82e4 W329Stop allele, and can be backcrossed with one of the parents, such as ALBEX1F or TN 90 if desired. In some aspects, a plant population in the $F_2$ generation is screened for a cyp82e4 W329Stop allele. Selected plants can be crossed with one of the parents and the first backcross (BC1) generation plants are self-pollinated to produce a $BC1F_2$ population that is again screened for variant nicotine demethylase gene expression (e.g., the null version of the nicotine demethylase gene). The process of backcrossing, self-pollination, and screening is repeated, for example, at least 4 times, until the final screening produces a plant that is fertile and reasonably similar to the recurrent parent. This plant, if desired, is self-pollinated and the progeny are subsequently screened again to confirm that the plant exhibits the same low nicotine conversion phenotype as ALBEX1F. Breeder's seed of the selected plant is produced using standard methods including, for example, field testing, confirmation of the null condition for nicotine demethylase, chemical analyses of cured leaf to determine the level of alkaloids and/or chemical analyses of cured leaf to determine the ratio of nornicotine to nicotine+ nornicotine.

In one aspect, a $F_1$ progeny is the result of a cross between ALBEX1F and ALBEX1MS to generate $F_1$ progeny that are male sterile. Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), Mac-Millan Publishing Go., Inc., New York, N.Y. 761 pp.

The present invention further provides methods of producing a tobacco plant by crossing one of cultivars ALBEX1F and ALBEX1MS with itself or a different tobacco line. The invention further relates to methods for producing other tobacco cultivars or breeding lines derived from cultivars ALBEX1F and ALBEX1MS by crossing a plant of cultivars ALBEX1F and ALBEX1MS with a second tobacco plant and growing the progeny seed to yield an ALBEX1F- or ALBEX1MS-derived tobacco plant. An additional aspect of the present invention provides a method for a tobacco plant that contains in its genetic material one or more transgenes, comprising crossing cultivars of the present invention with a second cultivar containing one or more transgenes wherein progeny are produced, so that the genetic material of the progeny that result from the cross comprise the transgene(s) optionally operably linked to one or more regulatory elements. In one aspect, the second cultivar may be a plant derived from cultivars ALBEX1F or ALBEX1MS transformed with one or more transgenes.

The invention further provides for the vegetative propagation of a plant of cultivars ALBEX1F and ALBEX1MS, hybrids and progeny thereof. In one aspect, the invention provides for a method of vegetatively propagating a plant of a tobacco cultivar comprising collecting tissue capable of being propagated from a plant of a plant of cultivars ALBEX1F and ALBEX1MS, cultivating the tissue to obtain a proliferated shoot and rooting the proliferated shoots to obtain a rooted plantlet. In another aspect, the plant tissue may be collected from an $F_1$ hybrid of a plant of cultivars ALBEX1F and ALBEX1MS. In an aspect, the plant tissue may be collected from an $F_2$, $F_3$, $F_4$ or later progeny plant obtained by breeding a plant of cultivars ALBEX1F and ALBEX1MS.

A plant comprising a mutation in a nicotine demethylase gene can be identified by selecting or screening the mutagenized plant material, or progeny thereof. Such screening and selection methodologies are known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

It is understood that a tobacco plant of the present invention, including ALBEX1F and ALBEX1MS, can be transformed by a genetic construct or transgene using a technique known in the art. Without limitation, an example of a desired trait is herbicide resistance, pest resistance, disease resistance; high yield; high grade index; curability; curing quality; mechanical harvestability; holding ability; leaf quality; height, plant maturation (e.g., early maturing, early to medium maturing, medium maturing, medium to late maturing, or late maturing); stalk size (e.g., a small, medium, or a large stalk); or leaf number per plant (e.g., a small (e.g., 5-10 leaves), medium (e.g., 11-15 leaves), or large (e.g., 16-21) number of leaves), or any combination. Any plant of the present invention can be used as a basis for tissue culture, regenerated, transformed, or a combination of any of these. In an aspect, a plant of the present invention derived by tissue culture, transformation, or both has essentially all of the morphological and physiological characteristics of cultivar ALBEX1F or ALBEX1MS grown under similar conditions.

Having now generally described the invention, the same will be more readily understood through reference to the following examples that are provided by way of illustration, and are not intended to be limiting of the present invention, unless specified.

EXAMPLES

Example 1

Breeding of Homozygous cyp82e4 W329Stop Mutant Plants into the TN 90 Background

ALBEX1F is a backcross-derived version of burley tobacco cultivar TN 90 carrying an introduced deleterious mutation in cyp82e4, a gene previously documented to encode for nicotine demethylase enzymes. To prepare ALBEX1F, an individual plant grown from a commercial seedlot of TN 90 is selected and initially crossed with plant 4246-8 in a greenhouse. 4246-8 is a tobacco cultivar heterozygous for the cyp82e4 W329Stop mutation. A plurality of $F_1$ plants are screened for the presence of the cyp82e4 W329Stop mutation. Individual $F_1$ plants are selected and backcrossed to TN 90 in a greenhouse to produce $BC_1F_1$ progeny. A plurality of $BC_1F_1$ progeny are screened and an individual plant heterozygous for the cyp82e4 W329Stop mutation is identified. The heterozygous selected $BC_1F_1$ plant is backcrossed to TN 90 in a greenhouse to produce $BC_2F_1$ seed. A plurality of $BC_2F_1$ plants are screened for the presence of the cyp82e4 W329Stop mutation to identify a heterozygous progeny plant for a subsequent round of backcross breeding. Using this backcross procedure, individual heterozygous plants having the cyp82e4 W329Stop mutation are identified in the $BC_3F_1$, $BC_4F_1$, and $BC_5F_1$ progeny.

To produce plants homozygous for the cyp82e4 W329Stop mutation, $BC_5F_1$ progeny plants are screened for the cyp82e4 W329Stop mutation to identify heterozygous plants. Individual plants heterozygous for the cyp82e4 W329Stop mutation are self-pollinated to produce $BC_5F_2$ seed. A plurality of $BC_5F_2$ progeny are genotyped to identify individuals homozygous for the cyp82e4 W329Stop mutation. Four individual $BC_5F_2$ progeny plants are self-pollinated to produce four $BC_5F_3$ progeny lines. $BC_5F_3$ are homozygous for the CYP82E4 W329Stop mutation.

Example 2

Preparation of Male Sterile Lines

To prepare a male sterile (MS) line, a progeny plant of the $BC_5F_1$ prepared in Example 1 (described above) that is heterozygous for the cyp82e4 W329Stop mutation is selected and crossed as the pollen parent to a MS TN 90. The MS $F_1$ progeny plants of the $BC_5F_1$×MS TN 90 cross are male sterile. These MS $F_1$ progeny plants (e.g., $BC_6F_1$ MS) are screened for the cyp82e4 W329Stop mutation. Similarly, the $BC_5F_1$ is crossed with a TN 90 to yield a fertile $BC_6F_1$ plant that is screened for the mutation. The MS $F_1$ progeny plant, identified as having the mutation, is the female parent in a subsequent cross with the fertile male parent $BC_6F_1$, which also has the mutation. Progeny of this cross (e.g., $BC_7F_1$ MS progeny) are male sterile and those that are homozygous for the cyp82e4 W329Stop mutation are identified by genotyping and designated as ALBEX1MS. To maintain the line, plants of line ALBEX1MS plants are pollinated with a ALBEX1F plant.

Example 3

Field Testing of ALBEX1MS Hybrid

Plants from the four ALBEX1MS progeny lines are grown in a randomized complete block design with three replications for evaluation of cured leaf chemistry, yield, and physical quality at the Blackstone field research location during 2010. Each replicated block is a 2-row plot with 25 plants per plot. Plants are stalk cut at maturity, air cured and evaluated by a former USDA tobacco grader. Plot weights are used to determine per acre yields. The fourth leaf from the top of twelve different test plants are collected to prepare a fifty gram composite leaf sample from each plot. Composite samples are analyzed for percent nicotine, nornicotine, anatabine, and anabasine by gas chromatography.

Analysis of ALBEX1MS Hybrid

The results of gas chromatography alkaloid analysis are presented in Table 1. Gas chromatography results are analyzed using JMP statistical software and a one-way analysis of variance is performed. The ALBEX1MS hybrid is found to not be significantly differed for different for nicotine, nornicotine, anabasine, anatabine, nicotine conversion, ratio of secondary alkaloids to total alkaloids, yield, or cured leaf quality.

TABLE 1

Comparisons between TN 90 and ALBEX1MS hybrid (TN 90 + e4e4) for alkaloid determinations, yield, and cured leaf quality.

| Entry | Plant Height (cm) | Grade Index | Yield (lbs/acre) | Nicotine (%) | Nornicotine (%) | Anabasine (%) | Anatabine (%) | Total Alkaloids (%) | Nicotine Conversion (%) |
|---|---|---|---|---|---|---|---|---|---|
| ALBEX1MS | 154.5 | 36.1 | 2814 | 4.84 | 0.138 | 0.0260 | 0.202 | 5.20 | 2.68% |
| TN 90 | 147.0 | 35.5 | 2974 | 4.99 | 0.162 | 0.0275 | 0.222 | 5.40 | 3.14% |
| p value | 0.1917 | 0.6340 | 0.4779 | 0.4236 | 0.2543 | 0.1340 | 0.1912 | 0.3442 | 0.3049 |

Means are from three 2010 Blackstone environments. The experimental design at each location was a randomized complete block design with three replications.
[a] P-values were obtained using JMP statistical software and a one-way analysis of variance.

Deposit Information

A deposit of at least 2500 seeds of the proprietary inbred plant lines disclosed above and recited in the appended claims have been made with American Type Culture Collection (ATCC), 10801 University Boulevard, Manassas, Va. 20110. The date of deposit for ALBEX1F and ALBEX1MS was Feb. 28, 2011 for both on behalf of Altria Client Services Inc. The deposit of 2500 seeds for each variety were taken from the same deposit maintained since prior to the filing date of this application. Upon issuance of a patent, all restrictions upon the deposit will be irrevocably removed, and the deposit is intended to meet all of the requirements of 37 C.F.R. §1.801-1.809. The ATCC accession numbers for inbred lines ALBEX1F and ALBEX1MS are, respectively, PTA-11716, and PTA-11717. These deposits will be maintained in the depository for a period of 30 years, or 5 years after the last request, or for the effective life of the patent, whichever is longer, and will be replaced as necessary during that period. Applicants do not waive any infringement of their rights granted under this patent or under the Plant Variety Protection Act (7 U.S.C. 2321 et seq.).

What is claimed is:

1. A seed of tobacco cultivar ALBEX1F, a tobacco cultivar essentially derived from said tobacco cultivar ALBEX1F, or a tobacco hybrid derived from said tobacco cultivar ALBEX1F, wherein said seed comprises SEQ ID NO: 1, a representative sample seed of said cultivar ALBEX1F is deposited with the ATCC under ATCC Accession No. PTA-11716.

2. A tobacco plant, or a part thereof, produced by growing the seed of claim 1, wherein said part is selected from the group consisting of leaf, pollen, ovule, embryo, cotyledon, hypocotyl, meristematic cell, protoplast, root, root tip, pistil, anther, flower, shoot, stem, pod and petiole.

3. A harvested leaf of the tobacco plant of claim 2.

4. The harvested leaf of claim 3, wherein said leaf has a reduced amount of nornicotine.

5. The harvested leaf of claim 4, wherein said reduced amount of nornicotine is reduced in a smoke stream produced from burning said leaf.

6. A tobacco product, prepared from the tobacco plant, or part thereof, of claim 2.

7. The tobacco product of claim 6, wherein said product is selected from the group consisting of a cigarillo, a non-ventilated recess filter cigarette, a vented recess filter cigarette, a cigar, snuff, pipe tobacco, cigar tobacco, cigarette tobacco, leaf tobacco, shredded tobacco, cut tobacco, and chewing tobacco.

8. The tobacco product of claim 7, wherein said product has a reduced amount of nornicotine.

9. A seed of tobacco cultivar ALBEX1MS, a tobacco cultivar essentially derived from said tobacco cultivar ALBEX1MS, or a tobacco hybrid derived from tobacco cultivar ALBEX1MS, wherein said seed comprises SEQ ID NO: 1, a representative sample seed of said cultivar ALBEX1MS is deposited with the ATCC under ATCC Accession No. PTA-11717.

10. A tobacco plant, or a part thereof, produced by growing the seed of claim 9, wherein said part is selected from the group consisting of leaf, pollen, ovule, embryo, cotyledon, hypocotyl, meristematic cell, protoplast, root, root tip, pistil, anther, flower, shoot, stem, pod and petiole.

11. A harvested leaf of the tobacco plant of claim 10.

12. The harvested leaf of claim 11, wherein said leaf has a reduced amount of nornicotine.

13. The harvested leaf of claim 12, wherein said reduced amount of nornicotine is reduced in a smoke stream produced from burning said leaf.

14. A tobacco product; prepared from the tobacco plant, or part thereof, of claim 10.

15. The tobacco product of claim 14, wherein said product is selected from the group consisting of a cigarillo, a non-ventilated recess filter cigarette, a vented recess filter cigarette, a cigar, snuff, pipe tobacco, cigar tobacco, cigarette tobacco, leaf tobacco, shredded tobacco, cut tobacco, and chewing tobacco.

16. The tobacco product of claim 15, wherein said product has a reduced amount of nornicotine.

17. An $F_2$ progeny plant of tobacco cultivar ALBEX1F, wherein said $F_2$ progeny plant comprises SEQ ID NO: 1, a representative sample seed of said cultivar is deposited with the ATCC under ATCC Accession No. PTA-11716.

18. An $F_2$ progeny plant of tobacco cultivar ALBEX1MS, wherein said $F_2$ progeny plant comprises SEQ ID NO: 1, a representative sample seed of said cultivar is deposited with the ATCC under ATCC Accession No. PTA-11717.

19. The $F_2$ progeny plant of claim 17, wherein said $F_2$ progeny plant is male sterile (MS).

20. The tobacco product of claim 6, wherein said tobacco product is prepared from said tobacco cultivar ALBEX1F or a tobacco hybrid derived from said tobacco cultivar ALBEX1F.

21. The tobacco product of claim 14, wherein said tobacco product is prepared from said tobacco cultivar ALBEX1MS or a tobacco hybrid derived from said tobacco cultivar ALBEX1MS.

* * * * *

SEQUENCE LISTING

<160> NUMBER OF SEQ ID NOS: 4

<210> SEQ ID NO 1
<211> LENGTH: 1751
<212> TYPE: DNA
<213> ORGANISM: Nicotiana tabacum

<400> SEQUENCE: 1

| aaggaagttg | ccgatagtta | tattctcaac | ttcttatcta | aaaatccata | atgctttctc | 60 |
| cccatagaagc | cattgtagga | ctagtaacct | tcacatttct | cttcttcttc | ctatggacaa | 120 |
| aaaaatctca | aaaaccttca | aaacccttac | caccgaaaat | ccccggagga | tggccggtaa | 180 |
| tcggccatct | tttccacttc | aatgacgacg | gcgacgaccg | tccattagct | cgaaaactcg | 240 |
| gagacttagc | tgacaaatac | ggccccgttt | tcacttttcg | gctaggcctt | cccttgtct | 300 |
| tagttgtaag | cagttacgaa | gctgtaaaag | actgtttctc | tacaaatgac | gccatttttt | 360 |
| ccaatcgtcc | agcttttctt | tacgcgatt | accttggcta | caataatgcc | atgctatttt | 420 |
| tggccaatta | cggaccttac | tggcgaaaaa | atcgaaaatt | agttattcag | gaagttctct | 480 |
| ccgctagtcg | tctcgaaaaa | ttcaaacacg | tgagatttgc | aagaattcaa | gcgagcatta | 540 |
| agaatttata | tactcgaatt | gatggaaatt | cgagtacgat | aaatttaact | gattggttag | 600 |
| aagaattgaa | ttttggtctg | atcgtgaaga | tgatcgctgg | aaaaaattat | gaatccggta | 660 |
| aaggagatga | acaagtggag | agatttaaga | aagcgtttaa | ggattttatg | attttatcaa | 720 |
| tggagtttgt | gttatgggat | gcatttccaa | ttccattatt | taaatgggtg | gatttttcaag | 780 |
| ggcatgttaa | ggctatgaaa | aggactttta | agatataga | ttctgttttt | cagaattggt | 840 |
| tagaggaaca | tattaataaa | agagaaaaaa | tggaggttaa | tgcagaaggg | aatgaacaag | 900 |
| atttcattga | tgtggtgctt | tcaaaaatga | gtaatgaata | tcttggtgaa | ggttactctc | 960 |
| gtgatactgt | cattaaagca | acggtgttta | gtttggtctt | ggatgcagca | gacacagttg | 1020 |
| ctcttcacat | aaattgagga | atggcattat | tgataaacaa | tcaaaaggcc | ttgacgaaag | 1080 |
| cacaagaaga | gatagacaca | aaagttggta | aggacagatg | ggtagaagag | agtgatatta | 1140 |
| aggatttggt | atacctccaa | gctattgtta | agaagtgtt | acgattatat | ccaccaggac | 1200 |
| ctttgttagt | accacacgaa | aatgtagaag | attgtgttgt | tagtggatat | cacattccta | 1260 |
| aagggacaag | attattcgca | aacgtcatga | aactgcaacg | tgatcctaaa | ctctggtctg | 1320 |
| atcctgatac | tttcgatcca | gagagattca | ttgctactga | tattgacttt | cgtggtcagt | 1380 |
| actataagta | tatcccgttt | ggttctggaa | gacgatcttg | tccagggatg | acttatgcat | 1440 |
| tgcaagtgga | acacttaaca | atggcacatt | tgatccaagg | tttcaattac | agaactccaa | 1500 |
| atgacgagcc | cttggatatg | aaggaaggtg | caggcataac | tatacgtaag | gtaaatcctg | 1560 |
| tggaactgat | aatagcgcct | cgcctggcac | ctgagcttta | ttaaaaccta | agatctttca | 1620 |
| tcttggttga | tcattgtata | atactcctaa | atggatattc | atttaccttt | tatcaattaa | 1680 |
| ttgtcagtac | gagttttttct | aatttggtac | atttgtaata | ataagtaaag | aataattgtg | 1740 |
| ctaatatata | a | | | | | 1751 |

<210> SEQ ID NO 2
<211> LENGTH: 328
<212> TYPE: PRT
<213> ORGANISM: Nicotiana tabacum

<400> SEQUENCE: 2

Met Leu Ser Pro Ile Glu Ala Ile Val Gly Leu Val Thr Phe Thr Phe

```
                1               5                    10                        15
        Leu Phe Phe Phe Leu Trp Thr Lys Lys Ser Gln Lys Pro Ser Lys Pro
                        20                   25                   30

Leu Pro Pro Lys Ile Pro Gly Gly Trp Pro Val Ile Gly His Leu Phe
                        35                   40                   45

His Phe Asn Asp Asp Gly Asp Arg Pro Leu Ala Arg Lys Leu Gly
                        50                   55                   60

Asp Leu Ala Asp Lys Tyr Gly Pro Val Phe Thr Phe Arg Leu Gly Leu
        65                       70                   75                   80

Pro Leu Val Leu Val Val Ser Ser Tyr Glu Ala Val Lys Asp Cys Phe
                                 85                   90                   95

Ser Thr Asn Asp Ala Ile Phe Ser Asn Arg Pro Ala Phe Leu Tyr Gly
                        100                  105                  110

Asp Tyr Leu Gly Tyr Asn Asn Ala Met Leu Phe Leu Ala Asn Tyr Gly
                        115                  120                  125

Pro Tyr Trp Arg Lys Asn Arg Lys Leu Val Ile Gln Glu Val Leu Ser
                        130                  135                  140

Ala Ser Arg Leu Glu Lys Phe Lys His Val Arg Phe Ala Arg Ile Gln
        145                      150                  155                  160

Ala Ser Ile Lys Asn Leu Tyr Thr Arg Ile Asp Gly Asn Ser Ser Thr
                        165                  170                  175

Ile Asn Leu Thr Asp Trp Leu Glu Glu Leu Asn Phe Gly Leu Ile Val
                        180                  185                  190

Lys Met Ile Ala Gly Lys Asn Tyr Glu Ser Gly Lys Gly Asp Glu Gln
                        195                  200                  205

Val Glu Arg Phe Lys Lys Ala Phe Lys Asp Phe Met Ile Leu Ser Met
                210                  215                  220

Glu Phe Val Leu Trp Asp Ala Phe Pro Ile Pro Leu Phe Lys Trp Val
        225                      230                  235                  240

Asp Phe Gln Gly His Val Lys Ala Met Lys Arg Thr Phe Lys Asp Ile
                        245                  250                  255

Asp Ser Val Phe Gln Asn Trp Leu Glu Glu His Ile Asn Lys Arg Glu
                        260                  265                  270

Lys Met Glu Val Asn Ala Glu Gly Asn Glu Gln Asp Phe Ile Asp Val
                275                  280                  285

Val Leu Ser Lys Met Ser Asn Glu Tyr Leu Gly Glu Gly Tyr Ser Arg
                290                  295                  300

Asp Thr Val Ile Lys Ala Thr Val Phe Ser Leu Val Leu Asp Ala Ala
        305                      310                  315                  320

Asp Thr Val Ala Leu His Ile Asn
                        325

<210> SEQ ID NO 3
<211> LENGTH: 1751
<212> TYPE: DNA
<213> ORGANISM: Nicotiana tabacum

<400> SEQUENCE: 3
aaggaagttg ccgatagtta tattctcaac ttcttatcta aaaatccata atgctttctc      60
ccatagaagc cattgtagga ctagtaacct tcacatttct cttcttcttc ctatggacaa     120
aaaaatctca aaaaccttca aaaccccttac caccgaaaat ccccggagga tggccggtaa    180
tcggccatct tttccacttc aatgacgacg gcgacgaccg tccattagct cgaaaactcg     240
gagacttagc tgacaaatac ggccccgttt tcactttcg gctaggcctt cccctgtct     300
```

```
tagttgtaag cagttacgaa gctgtaaaag actgtttctc tacaaatgac gccattttt      360
ccaatcgtcc agcttttctt tacggcgatt accttggcta caataatgcc atgctatttt     420
tggccaatta cggaccttac tggcgaaaaa atcgaaaatt agttattcag gaagttctct     480
ccgctagtcg tctcgaaaaa ttcaaacacg tgagatttgc aagaattcaa gcgagcatta    540
agaatttata tactcgaatt gatggaaatt cgagtacgat aaatttaact gattggttag    600
aagaattgaa ttttggtctg atcgtgaaga tgatcgctgg aaaaaattat gaatccggta    660
aaggagatga acaagtggag agatttaaga aagcgtttaa ggattttatg attttatcaa    720
tggagtttgt gttatgggat gcatttccaa ttccattatt taaatgggtg gattttcaag    780
ggcatgttaa ggctatgaaa aggactttta agatataga ttctgttttt cagaattggt     840
tagaggaaca tattaataaa agagaaaaaa tggaggttaa tgcagaaggg aatgaacaag    900
atttcattga tgtggtgctt tcaaaaatga gtaatgaata tcttggtgaa ggttactctc    960
gtgatactgt cattaaagca acggtgttta gtttggtctt ggatgcagca gacacagttg   1020
ctcttcacat aaatttgggga atggcattat tgataaacaa tcaaaaggcc ttgacgaaag   1080
cacaagaaga gatagacaca aaagttggta aggacagatg ggtagaagag agtgatatta   1140
aggatttggt atacctccaa gctattgtta agaagtgtt acgattatat ccaccaggac    1200
ctttgttagt accacacgaa aatgtagaag attgtgttgt tagtggatat cacattccta   1260
aagggacaag attattcgca aacgtcatga aactgcaacg tgatcctaaa ctctggtctg   1320
atcctgatac tttcgatcca gagagattca ttgctactga tattgacttt cgtggtcagt   1380
actataagta tatcccgttt ggttctggaa gacgatcttg tccagggatg acttatgcat   1440
tgcaagtgga acacttaaca atggcacatt tgatccaagg tttcaattac agaactccaa   1500
atgacgagcc cttggatatg aaggaaggtg caggcataac tatacgtaag gtaaatcctg   1560
tggaactgat aatagcgcct cgcctggcac ctgagcttta ttaaaaccta agatctttca   1620
tcttggttga tcattgtata atactcctaa atggatattc atttaccttt tatcaattaa   1680
ttgtcagtac gagttttct aatttggtac atttgtaata ataagtaaag ataattgtg    1740
ctaatatata a                                                        1751
```

<210> SEQ ID NO 4
<211> LENGTH: 517
<212> TYPE: PRT
<213> ORGANISM: Nicotiana tabacum

<400> SEQUENCE: 4

```
Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110
```

```
Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
            325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asp Pro Thr Phe Asp Pro Glu Arg
            420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
            485                 490                 495

Thr Ile Arg Lys Val Asn Pro Val Glu Leu Ile Ile Ala Pro Arg Leu
            500                 505                 510

Ala Pro Glu Leu Tyr
            515
```